US012629144B2

(12) United States Patent
Richards et al.

(10) Patent No.: US 12,629,144 B2
(45) **Date of Patent: *May 19, 2026**

(54) SYSTEMS AND METHODS INCLUDING AN ADJUSTABLE RETRACTOR FRAME

(71) Applicant: BIOPHYX SURGICAL, INC., Clawson, MI (US)

(72) Inventors: Robert Richards, Clawson, MI (US); Stephen Maguire, Shelton, CT (US)

(73) Assignee: BIOPHYX SURGICAL, INC., Clawson, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/667,779

(22) Filed: May 17, 2024

(65) Prior Publication Data

US 2024/0350132 A1 Oct. 24, 2024

Related U.S. Application Data

(63) Continuation of application No. 18/134,613, filed on Apr. 14, 2023, now Pat. No. 12,016,544, which is a (Continued)

(51) Int. Cl.
*A61B 17/02* (2006.01)
*A61B 1/32* (2006.01)
(Continued)

(52) U.S. Cl.
CPC ............ *A61B 17/0293* (2013.01); *A61B 1/32* (2013.01); *A61B 2017/00858* (2013.01); *A61B 2017/0287* (2013.01); *A61B 46/23* (2016.02)

(58) Field of Classification Search
CPC ... A61B 1/32; A61B 17/02; A61B 2017/0287; A61B 17/0293; A61B 46/00; A61B 46/20; A61B 2046/205; A61B 46/23
See application file for complete search history.

(56) References Cited

U.S. PATENT DOCUMENTS 2,845,925 A 8/1958 Jayle
4,430,991 A 2/1984 Darnell
(Continued)

FOREIGN PATENT DOCUMENTS

EP 2 873 376 2/2019
GB 2553313 3/2018
(Continued)

OTHER PUBLICATIONS

European Search Report EP21884067 dated Mar. 12, 2024.
(Continued)

*Primary Examiner* — Larry E Waggle, Jr.
(74) *Attorney, Agent, or Firm* — Neil D. Gershon

(57) ABSTRACT

A device for surgical retraction having a frame flexible to conform to a patient's anatomy, the frame including at least one anchoring member for retaining a tissue retraction member. A stabilizing member is attached to the frame and secures the stabilizing member to a patient, wherein a tissue retraction member applying a force to the frame in a first direction is counterbalanced by the stabilizing member to provide a force in a second opposite direction.

21 Claims, 24 Drawing Sheets

Related U.S. Application Data continuation-in-part of application No. 17/920,458, filed as application No. PCT/US2021/056510 on Oct. 25, 2021, now Pat. No. 11,819,202.

(60) Provisional application No. 63/134,782, filed on Jan. 7, 2021, provisional application No. 63/104,569, filed on Oct. 23, 2020.

(51) Int. Cl.
  *A61B 17/00*     (2006.01)
  *A61B 46/23*     (2016.01)

(56)                References Cited

U.S. PATENT DOCUMENTS

| | | | |
|---|---|---|---|
| 4,434,791 A | 3/1984 | Darnell | |
| 4,643,181 A | 2/1987 | Brown | |
| 5,161,544 A * | 11/1992 | Morris | A61B 46/30 |
| | | | 128/853 |
| 5,810,721 A | 9/1998 | Mueller et al. | |
| 5,951,467 A | 9/1999 | Picha et al. | |
| 5,964,697 A | 10/1999 | Fowler, Jr. | |
| 6,190,311 B1 | 2/2001 | Glines et al. | |
| 6,572,541 B1 | 6/2003 | Petersvik | |
| 6,659,945 B2 | 12/2003 | Ball et al. | |
| 6,705,324 B1 | 3/2004 | Petersvik | |
| 7,909,761 B2 * | 3/2011 | Banchieri | A61B 1/0676 |
| | | | 600/215 |
| 8,262,567 B2 | 9/2012 | Sharp et al. | |
| 8,517,995 B2 | 8/2013 | Voegele et al. | |
| 8,758,235 B2 | 6/2014 | Jaworek | |
| 8,857,440 B2 | 10/2014 | Gundlapalli et al. | |
| 11,819,202 B2 * | 11/2023 | Richards | A61B 1/32 |
| 12,016,544 B2 * | 6/2024 | Richards | A61B 46/40 |
| 2003/0055439 A1 | 3/2003 | Koseki | |
| 2004/0242969 A1 | 12/2004 | Sherts et al. | |
| 2005/0171404 A1 | 8/2005 | Mische | |
| 2007/0156023 A1 | 7/2007 | Frasier et al. | |
| 2007/0232864 A1 | 10/2007 | Sharp et al. | |
| 2007/0235038 A1 * | 10/2007 | Alinsod | A61B 17/02 |
| | | | 128/849 |
| 2011/0172495 A1 | 7/2011 | Armstrong | |
| 2014/0031632 A1 * | 1/2014 | Nakao | A61B 17/0206 |
| | | | 600/206 |
| 2018/0243039 A1 | 8/2018 | Ramires et al. | |

FOREIGN PATENT DOCUMENTS

| | | |
|---|---|---|
| WO | WO 2018/042159 | 3/2018 |
| WO | WO 2022/087537 | 4/2022 |

OTHER PUBLICATIONS

International Search Report and Written Opinion PCT/US21/56510, Dated Jan. 31, 2022.
International Search Report and Written Opinion PCT/US24/22704, Dated Aug. 22, 2024.

\* cited by examiner

210

(B) Adhesive film attached directly to skin (A) Adhesive film under 'peel'

SYSTEMS AND METHODS INCLUDING AN ADJUSTABLE RETRACTOR FRAME

CROSS REFERENCE TO RELATED APPLICATION(S)

This application is a continuation of application Ser. No. 18/134,613, filed Apr. 14, 2023, which is a continuation-in-part of application Ser. No. 17/920,458, filed Oct. 21, 2022, which is a 371 of international application no. PCT/US2021/056510, filed Oct. 25, 2021, which claims the benefit of U.S. Provisional Application Nos. 63/104,569, filed Oct. 23, 2020, and 63/134,782, filed Jan. 7, 2021. The entire contents of each of these applications are incorporated herein by reference.

BACKGROUND OF THE INVENTION

Field of the Invention

This application is directed to surgical retractor systems, and, more particularly, to retractor systems to accommodate various patient anatomy during surgical procedures.

Background

Surgery is rapidly changing in response to the need to reduce healthcare costs while at the same time reducing risk of infection and spread of viruses that can compromise patient safety. Surgery utilizes multiple force vectors applied to various tissues to apply various forms of retraction to allow access to a surgical site. In the most basic scenario, these tissue retractors are placed and held in position manually by surgeons and surgical assistants. This leads to compromised visualization of the operative site, compromised approach angles, and increased costs due to increased operating room staff and increased infection risk associated with additional personnel. Further, operator fatigue oftentimes leads to undesired placement or movement of retractors which requires revision by the surgeon leading to increased time under anesthesia and exposure and subsequently increased risk of adverse events. Furthermore, the requirement for intraoperative adjustments of anatomy presents challenges to the retraction techniques.

To mitigate the risks associated with human operators controlling retraction devices, there have been several attempts at non-manual retractor instruments that can minimize the number of personnel required in the operating room (reduced cost and risk). These devices include retractor frames and retractor components that engage with the tissue and attempt to provide retraction and adjustment of tissue by anchoring tissue to a relatively rigid frame that is placed around the operative site. However, it is common for such devices to compromise the surgical field visualization and access, need multiple hands for initial placement and readjustment of retractors, and commonly require repositioning during the procedure because they either inadvertently disengage from the site, or require repositioning, thereby complicating and prolonging the procedure. Mechanical holding arms that attach the retractor frame physically to the operating table aim to overcome some of these problems by preventing unintentional movement of the frame, but these add even more bulk and are difficult and time consuming to adjust if repositioning is required. Current retractor devices hinder the operation of surgical procedures which require the operated site be manipulated during the procedure. This is common, e.g., in shoulder surgery where the patient's arm is moved during the procedure. Further, repositioning of these traditional devices introduces risks of infection.

Additional attempts to solve these and similar problems include rigid metal retractor frames, typically anchored to the bed frame to allow for attachment of various tools to assist with retraction. Protective membranes, e.g., Ioban™ or Tegaderm™ surgical drapes, have been used to reduce infection at the surgical site. Single use disposable plastic frames are typically anchored to the surgical site by the placement of multiple elastic "stays." The latter is mostly used to retract the superficial soft tissue and is not capable of substantial retraction forces. Further, these frames are not capable of unilateral retraction, i.e., require balanced retraction vectors to maintain frame position. Thus, should the retraction forces become unbalanced, these retractors need to be repositioned. These rigid frames are rarely flush with the surface of the skin. There remain limitations to retractor frames including the ability to accommodate intraoperative motion required during some procedures such as joint surgery that may require range of motion trialing. Additionally, retractor frames that are not affixed to the patient can be unstable.

The limitations of the current state of the retractor systems illustrates the need for a system suitable for anatomic repositioning mid-case, i.e., intraoperatively.

Consequently, the need exists for a retractor system to address the deficiencies of prior retractor systems. That is, the need exists for a retractor system that can conform to various patient anatomies, accommodates substantial retraction forces, reduces the need for repositioning of the retractor during the surgical procedure and effectively retracts various types of tissue without adversely affecting visualization of the surgical site and without adding additional bulk.

SUMMARY OF THE INVENTION

The retractor systems of the present invention overcome the disadvantages and deficiencies of the prior art. The retractor systems of the present invention have one or more of the following advantages: 1) accommodate substantial retraction forces; 2) reduce the need for repositioning of the retractor during the surgical procedure; 3) effectively retract various types of tissue; 4) are sufficiently flexible to accommodate various anatomical curvatures; 5) effectively accommodate intraoperative motion during surgical procedures; 6) do not adversely affect visualization of the surgical site; and/or 7) are sufficiently streamlined so is less bulky.

Various embodiments of the retractor systems of the present invention to provide surgical retraction with one or more of the foregoing advantages are described in detail below.

In some embodiments, the retractor of the present invention can be removed and relocated or removed and replaced with a new retractor intraoperatively. This retractor replacement system is discussed in detail below.

The retractors of the present invention in some embodiments are configured to maintain the integrity and stability of the grooves/notches that support tissue retraction devices to enhance securement of the retraction devices. This is also explained in more detail below.

In some embodiments, the retractor has specific rigid and flexible segments to effectively strike the balance between sufficient flexibility and sufficient rigidity of the system.

In accordance with one aspect of the present invention, the system includes a frame composed of one or more flexible materials, the frame including a plurality of anchor points and at least one stabilizing member having one or more securing apparatus applied thereto to prevent motion of the system relative to a surgical site.

In some embodiments, a securing apparatus is positioned outside of a perimeter of the frame and a securing apparatus is positioned inside of the perimeter of the frame. In some embodiments, the frame is composed of a biocompatible material, such as nylon, 304 annealed stainless steel, or combinations thereof.

In some embodiments, one or more of the at least one stabilizing member includes one or more features that are positioned on, under, or in, the one or more securing apparatus, or combinations thereof, the one or more features configured to provide tensile and compressive load resistance.

In some embodiments, at least one stabilizing member extends outwardly from the perimeter of the frame; in other embodiments the at least one stabilizing member extends inwardly from the perimeter of the frame; with and in other embodiments, the at least one stabilizing member extends both outwardly and inwardly from the frame.

In some embodiments, one or more of the at least one stabilizing members includes a sheet integrated with the frame, one or more of the at least one stabilizing members, or combinations thereof. In some embodiments, the sheet includes one or more antimicrobial agents. In some embodiments, the sheet extends inwardly from the perimeter of the frame and is configured to be cuttable via a scalpel or alternatively have an opening to a surgical site. In some embodiments, the securing apparatus includes an adhesive layer, a friction fit, gravity, suction, magnets, or combinations thereof.

In accordance with another aspect of the present invention, a system for providing surgical retraction is provided including a frame composed of one or more flexible materials, the frame including a plurality of anchor points positioned around a perimeter thereof, and a plurality of stabilizing members extending from the frame, the stabilizing members including one or more adhesive layers to prevent motion of the system relative to a surgical site.

In some embodiments, a stabilizing member extends outwardly from the perimeter of the frame and a stabilizing member extends inwardly from the perimeter of the frame. In some embodiments, the frame allows deformation in a plane substantially perpendicular to a surface of a patient's anatomy at the surgical site but resists deformation in a plane substantially parallel to the surface.

In some embodiments, the stabilizing members have a thickness gradient along an axis thereof. In some embodiments, the at least one stabilizing member includes a sheet extending outwardly from the perimeter of the frame, inwardly from the perimeter of the frame, or combinations thereof, and at least one feature extending outwardly from the perimeter of the frame, inwardly from the perimeter of the frame, or combinations thereof. In some embodiments, the sheet has a thickness between about 30 µm and about 100 µm and the at least one features have a thickness between about 100 µm, and about 0.5 cm. In some embodiments, the sheet extends inwardly from the perimeter of the frame to completely cover an interior space defined by the perimeter.

In some embodiments, the anchor points maintain or substantially maintain their configuration during flexing or bending of the retractor frame.

In accordance with another aspect of the present invention, a system for providing surgical retraction is provided that includes a frame including a perimeter, a first surface, and a second surface facing opposite the first surface. A plurality of anchor points (anchor members) are positioned around the perimeter. The system further includes at least one stabilizing member. In some embodiments, the system includes an adhesive layer applied to the second surface, the stabilizing members, or combinations thereof, the adhesive layer configured to reversibly adhere the system to a surface of a patient's anatomy or to a surface, e.g., a surgical drape, overlying the patient's anatomy.

In some embodiments, the at least one stabilizing member extends at least laterally inwardly from the perimeter of the frame. In some embodiments, the adhesive layer extends laterally outwardly from the perimeter of the frame and laterally inwardly from the perimeter of the frame. In some embodiments, the frame allows deformation in a plane substantially perpendicular to a surface of a patient's anatomy at the surgical site but resists deformation in a plane substantially parallel to the surface.

In some embodiments, one or more of the at least one stabilizing member includes one or more features positioned on, under, or in the one or more adhesive layers, or combinations thereof, to prevent motion of the adhesive layer, the one or more features configured to provide tensile and compressive load resistance. The one or more features can include elongated sections having a generally lattice-shaped construction. In some embodiments, the at least one stabilizing member includes a sheet extending laterally outwardly from the perimeter of the frame, laterally inwardly from the perimeter of the frame, or both inwardly and outwardly from the frame. In some embodiments, the sheet extends inwardly from the perimeter of the frame to completely cover an interior space defined by the perimeter. In some embodiments, the sheet includes one or more antimicrobial agents.

In accordance with another aspect of the present invention, a device for surgical retraction is provided comprising a frame having a lower surface, and opposing upper surface and a periphery defining an interior space, the frame including at least one anchor point extending therefrom for retaining a tissue retraction member, the frame flexible to conform to a patient's anatomy. A stabilizing member is attached to the frame adhesively adhering to a skin of the patient or a surface overlying the skin of a patient to secure the frame, the stabilizing member extending underneath the frame. The stabilizing member and adhesive extend laterally outwardly from the periphery of the frame and laterally inwardly from the periphery of the frame toward an incision site into the interior space to thereby provide an adherence surface to an area larger than an area covered by the frame.

In accordance with another aspect of the present invention, a device for surgical retraction is provided comprising a frame having a periphery, a lower surface and an opposing upper surface, the frame including at least one anchor point extending therefrom for retaining a tissue retraction member, the frame flexible to conform to a patient's anatomy. A stabilizing member is attached to the frame, the stabilizing member adhesively adhering to a skin of the patient or a surface overlying the skin of a patient to secure the frame. The frame is configured to allow deformation in a plane perpendicular to a surface of the anatomy and resist deformation in a plane parallel to the surface of the anatomy.

In accordance with another aspect of the present invention, a surgical retraction system for providing surgical retraction is provided comprising a frame having a periphery, a bottom surface and an opposing upper surface, the frame including at least one anchor point extending therefrom for retaining a tissue retraction member, the frame flexible to conform to a patient's anatomy. A stabilizing member is attached to the frame, the stabilizing member adhesively adhering to a skin of the patient or a surface overlying the skin of a patient to secure the frame. The stabilizing member is configured to remain anchored to the surface of the anatomy while the frame deforms to conform to the patient's anatomy.

In accordance with another aspect of the present invention, a surgical retraction system for providing surgical retraction is provided comprising a frame including a plurality of interlocking segments including a plurality of end lock sections configured to reversibly engage with adjacent interlocking sections and a plurality of spline shafts inserted through engaged interlocking end lock sections of adjacent segments. The spline shafts have a first configuration permitting rotation of adjacent interlocking segments and a second configuration substantially preventing rotation of adjacent interlocking segments to rigidify the system. In some embodiments, the system further comprises one or more turret bases disposed in a first surface of the segments and a plurality of frame augmentations configured to reversibly attach to the frame via at least one of the one or more turret bases. In some embodiments, the frame augmentations include one or more anchor points, turret towers, suture locks, suction tube holders, retractor instrument holders, powered illuminated components, or combinations thereof for attachment of surgical devices, such as tissue retraction devices or suction devices, to the frame.

In accordance with another aspect, a device for surgical retraction is provided comprising a frame having a lower surface, and opposing upper surface and a periphery defining an interior space, the frame being flexible to conform to a patient's anatomy. The frame includes at least one anchoring member for retaining a tissue retraction member. A stabilizing member is attached to the frame and adhesively secures the device to a patient, wherein a tissue retraction member applying a force to the frame in a first direction is counterbalanced by the stabilizing member to provide a force in a second opposite direction.

In some embodiments, net forces defined by simultaneous force in the first direction and second direction are zero.

In some embodiments, the stabilizing member extends underneath the frame, the stabilizing member extending laterally outwardly from the periphery of the frame and laterally inwardly from the periphery of the frame toward an incision site into the interior space to thereby provide an adherence surface to an area larger than an area covered by the frame.

In some embodiments, the frame is non-circular in configuration and has a first side and a second side opposite the first side, each side having first and second rigid sections and a flexible section between the first and second rigid sections. The frame can have a rigid section on each side between the first and second flexible sections. In some embodiments, corners of the frame are more rigid than the flexible sections.

In some embodiments, the at least one anchoring member is positioned at the first rigid section of the frame.

In some embodiments, the at least one anchoring member comprises a notch configured to frictionally retain a tissue retraction member, the notch having a V-shape tapering in a direction toward the stabilizing member. Preferably, the notch is configured to not open further during flexing of the frame enhance securement of the tissue retraction member.

In some embodiments, the stabilizing member includes antimicrobial agents carried thereon.

In some embodiments, the at least one anchoring member comprises a plurality of fingers spaced apart about the periphery and configured to frictionally maintain the tissue retraction members between the fingers and the at least one anchoring member extends laterally outwardly of an outermost edge of the frame and in a direction non-parallel to a plane of the frame.

In some embodiments, the stabilization (stabilizing) member has a region inward of the frame that can be cut, i.e., is incisable, by the surgeon to access the surgical site.

In some embodiments, the device further comprises a removable protective layer, the protective layer removable to expose the adhesive for securement of the device to skin of a patient or to a surgical drape positioned over the patient.

In some embodiments, the frame is configured to allow deformation in a plane perpendicular to a surface of the patient's anatomy and resist deformation in a plane parallel to the surface of the patient's anatomy.

In accordance with another aspect of the present invention, a device for surgical retraction is provided comprising a frame having a periphery, a lower surface and an opposing upper surface. The frame includes at least one anchor member extending therefrom for retaining a tissue retraction member, the frame flexible to conform to a patient's anatomy. A stabilizing member is attached to the frame, the stabilizing member adhering to a skin of the patient or a surface overlying the skin of a patient to secure the frame. The at least one anchoring member includes a notch (groove) to frictionally engage the tissue retraction member, the notch configured such that it is does not open further during flexing of the frame. In some embodiments, the notch is formed in a rigid section of the frame adjacent a living hinge of the frame. In some embodiments, the notch tapers in a direction toward the stabilizing member.

In accordance with another aspect of the present invention, a device for surgical retraction is provided comprising a frame having a periphery, a bottom surface and an upper surface opposing the bottom surface. The frame is flexible to conform to a patient's anatomy. The frame includes at least one anchor member extending therefrom for retaining a tissue retraction member. A stabilizing member is attached to the frame, the stabilizing member having a top layer and a bottom layer, the bottom layer adhesively adhering to a skin of the patient or a surface overlying the skin of a patient to secure the frame and the top layer is positioned between the bottom layer and the frame.

In some embodiments, the top layer is removable from the bottom layer to remove the frame, leaving the bottom layer of the stabilizing member adhesively adhered to the skin to the surface so that a second frame can be attached to the bottom layer to replace the first frame.

In some embodiments, the top layer is adhered to the bottom layer by surface tension, although other ways of attachment are also contemplated.

In some embodiments the bottom layer or top and bottom layer is or incisable to access the surgical site.

BRIEF DESCRIPTION OF THE DRAWINGS

The drawings show embodiments of the disclosed subject matter for the purpose of illustrating the invention. However, it should be understood that the present application is not limited to the precise arrangements and instrumentalities shown in the drawings. According to common practice, the drawings may not be to-scale, and the dimensions illustrated may be arbitrarily expanded or reduced. Additionally, certain components, elements, and/or features may be omitted from certain drawings (e.g., in the interest of clarity).

FIGS. 18A-18F are side schematic views illustrating a two layer adhesive protective layer wherein:

FIG. 18A illustrates the first and second peel away layers covering the adhesive surface;

FIG. 18B illustrates the first peel away layer being removed by pulling on the tab of the layer;

FIG. 18C illustrates the first peel away layer removed from the adhesive surface to expose the adhesive surface, the second peel away layer still protecting the underlying adhesive layer;

FIG. 18D illustrates one side of the second peel away layer being removed from the adhesive layer by pulling on the tab of the second layer to expose the underlying adhesive surface;

FIG. 18E illustrates a second side of the second peel away layer being removed by pulling on the tab to expose the underlying adhesive surface; and FIG. 18F illustrates the second side of the second peel away layer removed to expose the underlying adhesive surface.

DETAILED DESCRIPTION

The retractor systems of the present invention overcome the disadvantages and deficiencies of the prior art. The retractor systems of the present invention have one or more of the following features/advantages: 1) accommodate substantial retraction forces; 2) reduce the need for repositioning of the retractor during the surgical procedure; 3) effectively retract various types of tissue, e.g. deep and soft tissue; 4) are sufficiently flexible to accommodate various anatomical curvatures while providing sufficient stability so for example if a surgeon bumps it, it doesn't fail and is stable under dynamic loading, e.g., if an organ is pulled deep to one side, the retractor remains positioned over the wound and is stable for a period of time, e.g., during the entire surgical procedure if necessary; 5) effectively accommodate intra-operative motion during surgical procedures; 6) do not adversely affect visualization of the surgical site; and/or 7) provide a low profile design and are sufficiently streamlined so are less bulky. It should be appreciated that each of the aforementioned features/advantages provide an improvement over prior and current devices so that the present invention in some embodiments can have less than all of the seven listed features/advantages (e.g., only one, only two, etc.) and still provide an improved retractor system for surgical procedures.

The retractor of the present invention also advantageously strikes the balance between sufficiently flexible for conformance to patient's anatomy with sufficient stability to prevent unwanted movement or failure and resist torsion as well as transfer forces through the frame. Thus, the combination of the flexible frame with the stabilizing (stability) member allows for the strength of a rigid frame with the ablility to conform to the patient anatomy. The combination of the flexible frame with the stabilizing member also allows for unilateral retraction as the frame is anchored to the patient.

The retractor frame in some embodiments has rigid segments adjacent flexible segments. The rigid segment(s) does not deform when the retractor it is molded (deformed) to the patient, allowing it to maintain the attachment geometry and the flexible segment (the bridge FIG. 3; joint FIG. 4) allows for patient conforming. A wider bridge between the rigid sections prevents buckling. These segments are discussed in detail below.

Further, as described below, the frame includes slots and/or turret holes to secure retracting instruments attached to the frame. These in some embodiments are configured to remain unchanged while the device conforms to the patient's anatomy.

The retractors in some embodiments of the present invention have a drape protection layer, also referred to herein as "rescue drape." This enables easy removal of the retractor without damaging the drape. This is also discussed in detail below.

Figure 1A:
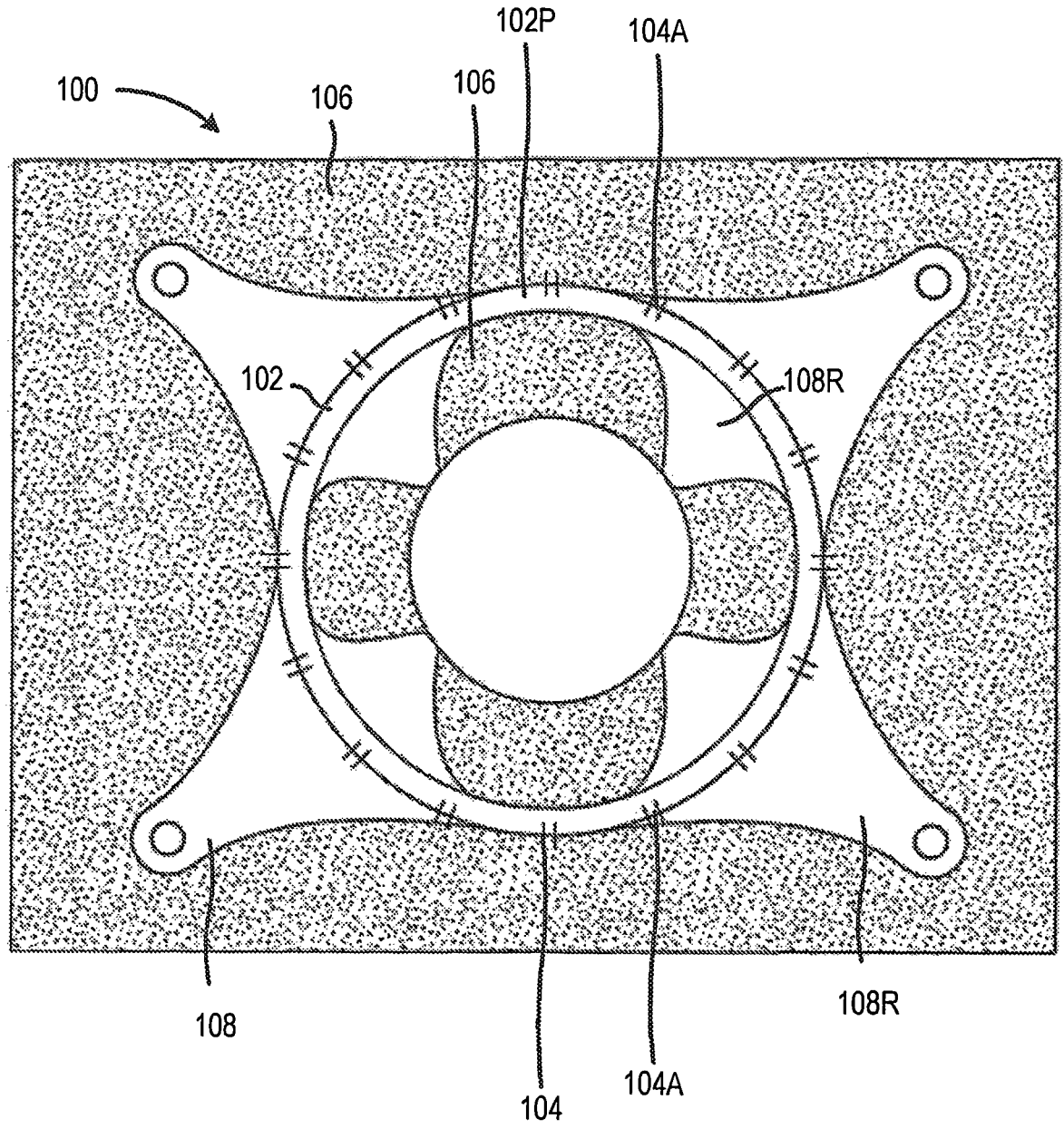
FIGS. 1A, 1B and 1C are each top schematic views of a system for providing surgical retraction according to some embodiments of the present disclosure.
Figure 1B:
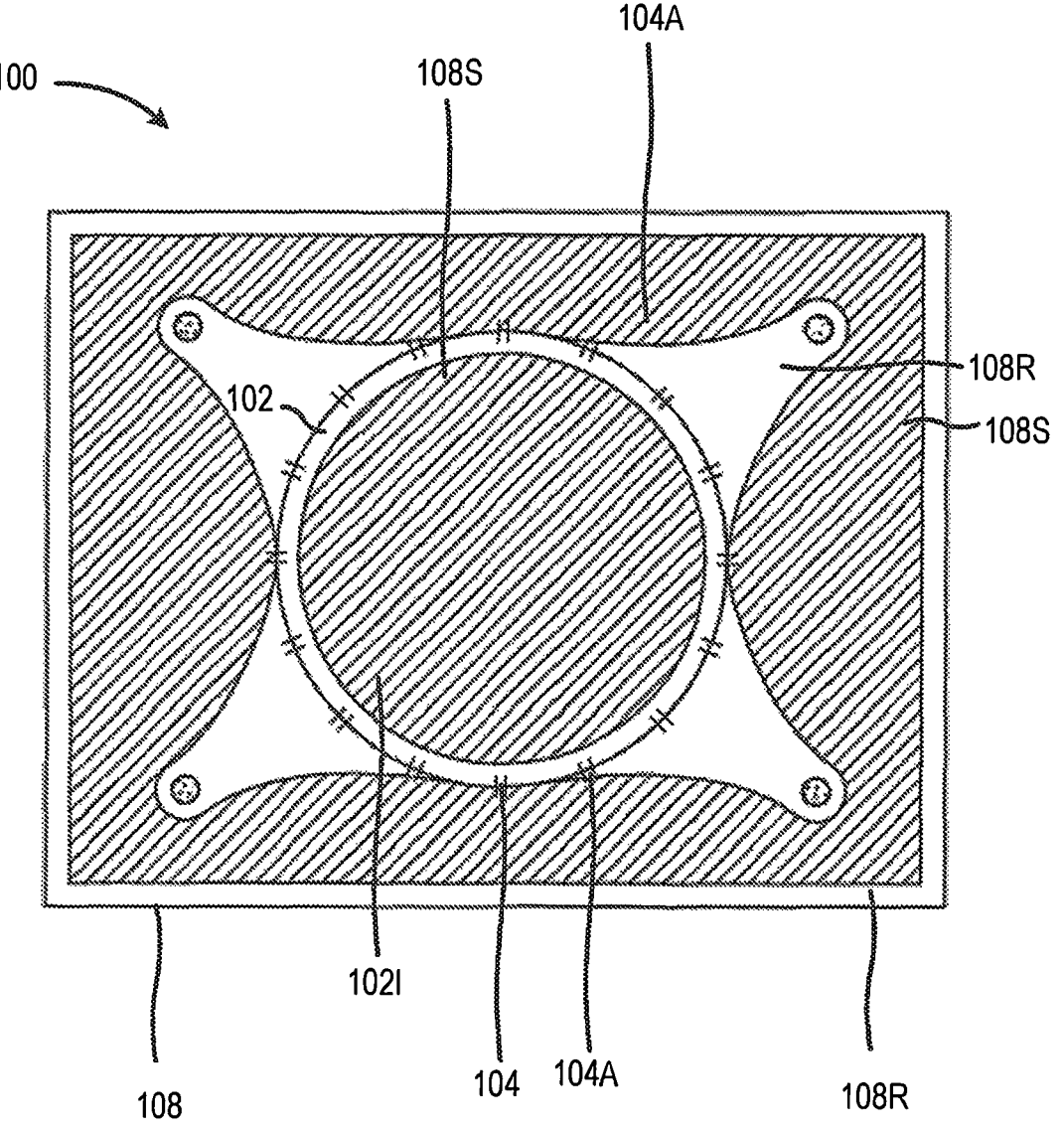
Figure 1C:
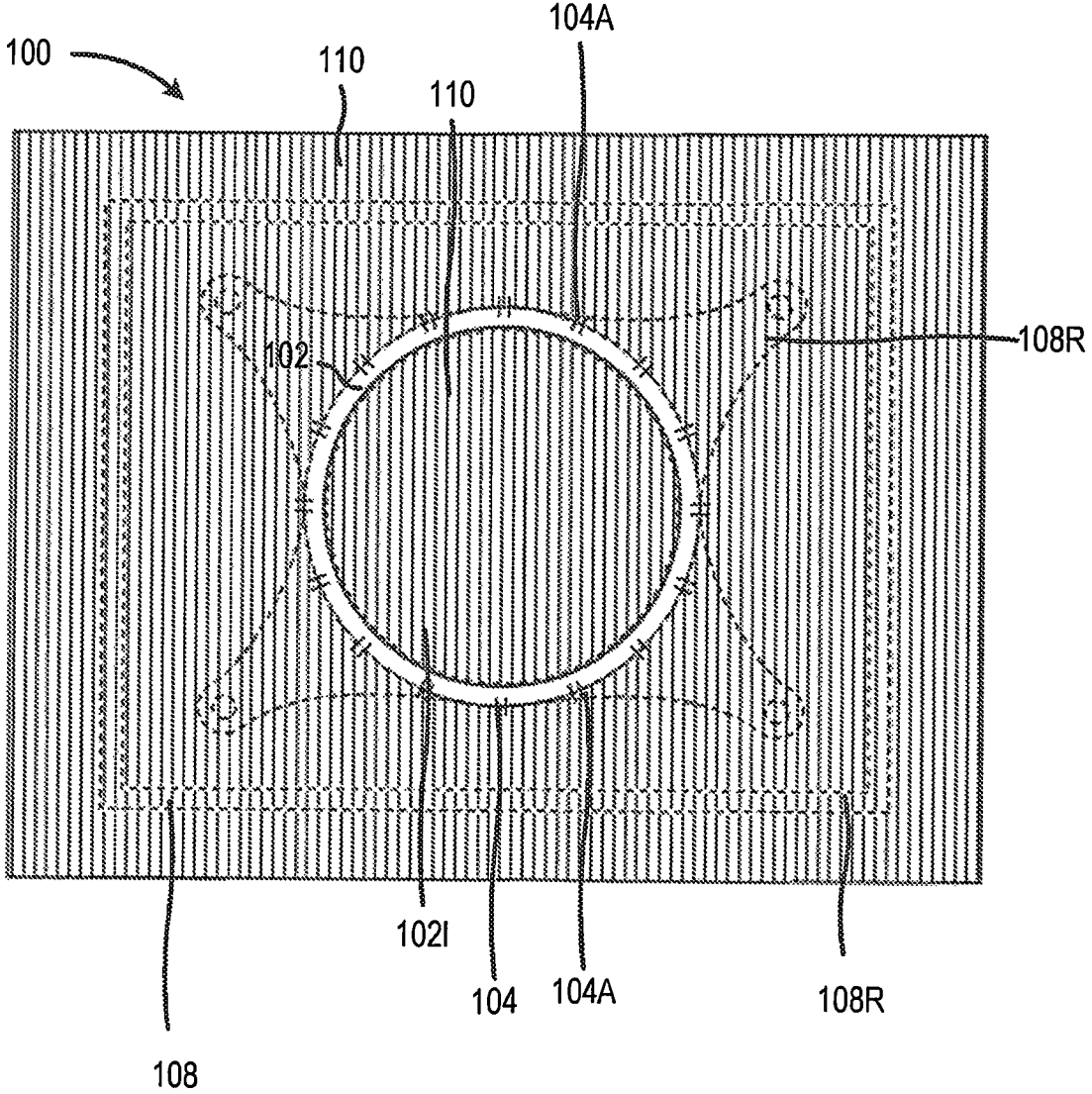
Figure 1D:
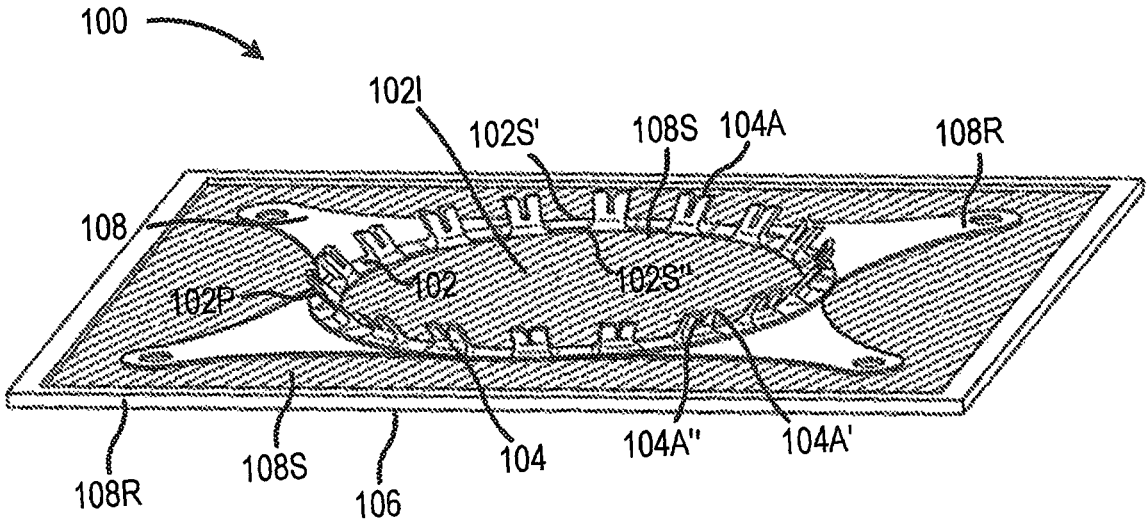
FIGS. 1D and 1E are isometric schematic views of the system of FIGS. 1A-1C.
Figure 1E:
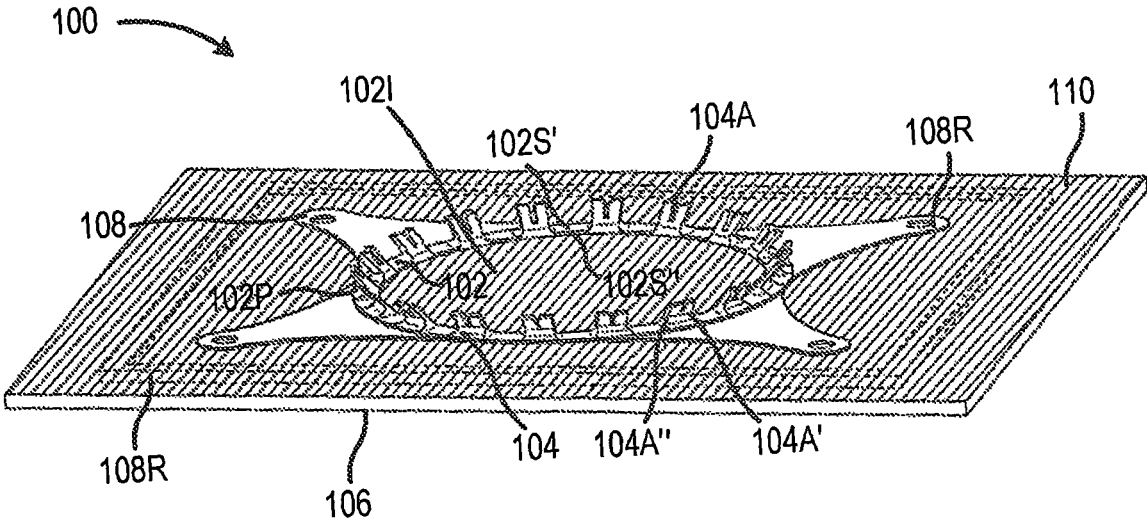

Referring now to the drawings and particular embodiments of the present disclosure, wherein like reference numerals identify similar structural features of the devices throughout the several views, and with initial reference to FIGS. 1A-1E, a retractor system of the present invention for providing retraction at a surgical site is illustrated and designated generally by reference numeral 100. The system 100 includes a frame 102 configured to conform to a patient's specific anatomy, e.g., a surface of the patient's skin, surgical drapes or other surfaces overlying the patient's skin, and the like, or combinations thereof. Frame 102 is configured to conform to the patient's anatomy, while also stabilizing one or more surgical tools during surgery, as will be discussed in greater detail below. In some embodiments, frame 102 is in the shape of a ring as shown in FIG. 1A, i.e., circular or substantially circular in shape, however it is envisioned that other configurations of the frame are also contemplated such as an oval as well as open shapes such as a segment of a circle, a segment of an oval, U-shape, a linear shape such as a linearly extending or angled bar shape, etc. In the embodiment of FIG. 11, the device has a configuration that is non-circular and somewhat square like with non-straight (curved) sides. In circular designs, bending in more than one axis is less optimal in certain anatomy. By providing the frame with rigid sections, the axis that each of the rigid sections will bend on is basically a line drawn between the two rigid sections and perpendicular to it (see lines of FIG. 10). The angles for certain clinical applications are preferably close to about 90 degrees as too small of an angle, e.g., 45 degrees, could limit its ability to bend over the skin in such certain clinical applications.

With continued reference to FIGS. 1A-1E, frame 102 includes a perimeter 102P, a first surface 102S', and a second surface 102S" which opposes first surface 102S', e.g., faces opposite the first surface. As shown, surface 102S' faces away from the patient and surface 102S" faces toward the patient. Perimeter 102P defines an interior space 1021, e.g., a circular frame defines the circular shaped space encircled by the frame, a U-shaped frame defines a space from the rounded base to the ends thereof, etc. That is, the interior space 1021 is defined within the confines of the frame.

Frame 102 is of sufficient thickness and flexibility for use at a particular surgical site, e.g., more rigid for spinal surgeries and more flexible for neck surgeries. The frame is composed of a biocompatible material and in preferred embodiments is composed of one or more flexible materials. Frame 102 can be composed of one or more biocompatible polymers, metals, or combinations thereof. In some embodiments, frame 102 is composed of nylon, 304 annealed stainless steel, or combinations thereof.

Frame 102 can include at least one coating layer, e.g., a soft rubberized material for better comfort and integration with a sheet.

In preferred embodiments, frame 102 allows deformation in a plane substantially perpendicular to a surface of a patient's anatomy at the surgical site but resists deformation in a plane substantially parallel to the surface, as will be discussed in greater detail below.

Still referring now to FIGS. 1A-1E, frame 102 includes one or more anchor points 104 positioned around perimeter 102P of frame 102. The anchor points can be spaced apart as shown. They can be equidistantly spaced around the perimeter 102P or alternatively some or all can be spaced at varying distances from one another. The number of anchor points can be more or less than the number shown in FIG. 1D and can extend around the entire perimeter or around only portions of the perimeter.

The anchor points can include one or more elastic anchor points or one or more rigid anchor points, or a combination of elastic and rigid anchor points such that frame 102 includes a plurality of elastic anchor points and a plurality of rigid anchor points. Anchor points 104 enable the attachment of various tools, e.g., rigid retractor arms, elastic band retractors (such as the Lonestar Stays), to retract tissue at the site, or additionally or alternatively for attachment of other instrument attachments, while enabling a clear view during surgery. Anchor points 104 can be of any suitable shape so long as they are able to maintain the position of tools attached to frame 102 in a desired location, e.g., relative to a surgical sites. The anchor points in some embodiments include V-shaped notches which are configured to maintain or substantially maintain their shape during bending or flexing of the retractor frame. This configuration is discussed in detail below in conjunction with FIGS. 13 and 14. The anchor points 104 are also referred to herein as anchoring members.

In some embodiments, tools are maintained in position by a friction fit with one or more anchor points 104, mechanical locking, e.g., bayonet, interference fit, etc., or combinations thereof, as will be discussed in greater detail below. In the illustrated embodiment, anchor points 104 include one or more prongs 104A which include a first finger 104A' and an adjacent second finger 104A". As shown, prongs 104A, e.g., first finger 104A' and second finger 104A", extend from frame 102 in a direction non-parallel to the plane of the frame. In some embodiments, prongs 104A extend from frame 102 in a direction no more than about 15 degrees from the surface of the patient's skin, although other angles are contemplated including angles parallel to the plane of the frame and perpendicular to the plane of the frame. In some embodiments, one or more tools are maintained in a desired position relative to a desired location via a friction fit between first finger 104A' and second finger 104A". In some embodiments, first finger 104A' and second finger 104A" extend a distance from frame 102 to provide sufficient surface area between them to allow for a friction fit with a desired tool, e.g., an elastic band retractor.

The frame geometry is a combination of flexible sections and rigid sections. This is shown for example in FIGS. 11 and 12 which illustrate an alternate shape of the retractor, but it should be understood that such rigid and flexible sections can be provided in the other frame shapes disclosed herein. The living hinges of retractor 200 provide the flexibility. Note that flexible joints provide the flexibility (flexible sections) in the below described embodiments of FIGS. 4-7 with interlocking segments. The placement of the hinges in both designs enables the advantageous anatomical conformance of the frame. The hinges allow movement in either direction (flex upwards or downwards) preferably by at least 30 degrees. Different anatomies can be accommodated by specific placement of the hinges around the periphery of the frame. For example, head and neck anatomy requires bending in two major planes, so locating the hinges centered around the 12/3/6/9 o'clock positions facilitates this anatomical conformance. Conversely, a more cylindrical anatomy (such as the lateral torso) requires bending in one major plane. In the embodiment of FIGS. 1-3, this can be accommodated by primarily a 12/6 o'clock hinge placement; in the embodiments of FIGS. 4-7, the user has the ability to conform then lock the frame in position in multiple or single planes.

The design of the living hinge advantageously enables the anatomical conformance and strength of the frame once placed in its anatomical position. The living hinge is characterized by its material and the thickness, width and length. Like a beam, these three characteristics are tuned in the retractors of the present invention to provide for the optimized combination of strength to resist the loads of retraction while still providing adequate flexibility where needed for anatomical conformance. Area Moment of Inertia (I) calculations are used to optimize the design of the living hinge.

The Area Moment of Inertia for a rectangular section can be calculated as:

$$I_x = b\,h^3/12$$

where $$b = \text{width}$$

$$h = \text{height}$$

Through both analytical and empirical evaluations, the inventors of the present invention have concluded that the I for optimal balance of strength and anatomical conformance is between 6.8E-2 mm$^4$ and 22.95E-2 mm$^4$ (((0.4^3)* (12.75))/12 to ((0.6^3)*(12.75))/12.

The living hinges allow for bending in two primary planes as can be appreciated by reference to retractor 200 of FIGS. 11 and 12. Living hinges 204 of frame 202 are located between rigid sections 206 on each of the four sides of the retractor. The corners 208 are also rigid and resist torsion of the sides, i.e., torsion out of the plane of the retractor. That is, the rigid corners 208 resist the tendency for the living hinges to be able to 'torque' into the page as viewed in FIG. 12. The primary bending planes are designated by lines C and D. The rigid sections 206 between the living hinges (flexible sections) 204 allow for retractor placement without compromising the 'V' groove that fits the retractors. Note for clarity only some of the rigid sections and flexible sections, i.e., living hinges, are labeled in the drawings, it being understood in preferred embodiments, each of the sides has a series of rigid sections, each separated by flexible sections to add flexibility. Also, the retractors of the other embodiments disclosed herein, e.g., of the other shapes, also preferably have living hinges (flexible sections) between rigid sections on its sides and rigid sections at the corners. Note that FIG. 11 shows retractor frame 202 without the stabilizing member for illustrative purposes; FIG. 12 shows retractor frame 202 with underlying stability (stabilizing) member 203.

Stated another way, the rigid frames allow for retractor attachment based on their ability to withstand the loads through a rigid structure. But they are rarely flush with the surface of the skin and cannot alone allow for unilateral retraction. The flexible frame plus the stabilizing (stability) member allows for strength of rigid frame with the ability to conform to patient anatomy. The frame plus the stabilizing member allows for unilateral retraction as the frame is anchored to the patient and the stabilizing member provides counterforces as described herein. This can be appreciated with reference to the arrows of FIG. 12 with arrow F showing by of example a direction of unilateral retraction and the multiple arrows G pointing in the opposite direction resisting the loads from the retractor frame. To appreciate the role of the stabilizing member, it should be appreciated that if unilateral retraction is applied to the frame without anything stabilizing it, the frame would move in the direction of the unilateral retraction force. Without a stabilizing member, the frame needs to have a retractor force that is balanced to prevent movement, meaning the net forces need to be zero. This leads to unnecessary or less desirable retractor placement to achieve balance as well as the inability to achieve unilateral (one sided) retraction. The stabilizing member of the retractors of the present invention solve this problem.

Figure 13:
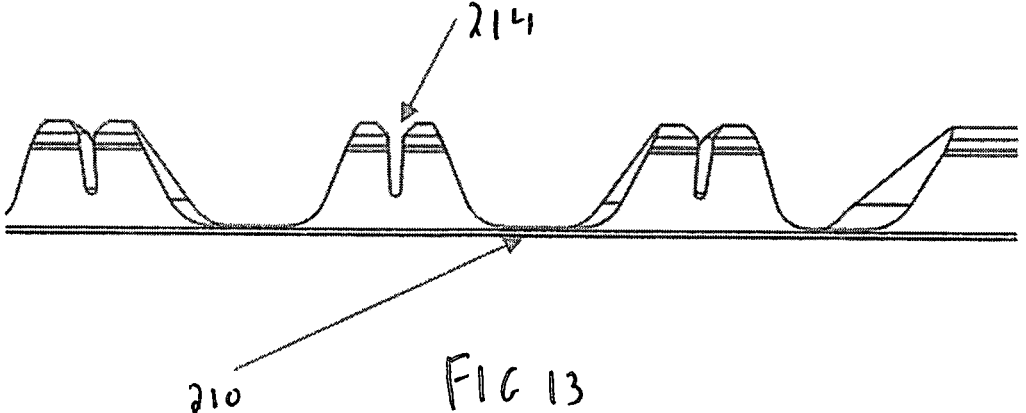
FIGS. 13 and 14 are close-up view of the V-notches of the frame of FIG. 11 for securing tissue retractors.
Figure 14:
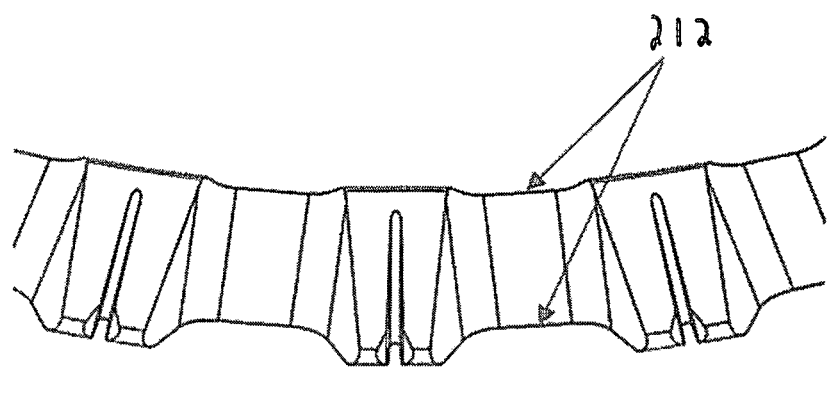

The frame geometry also provides a stable anchoring geometry for elastomeric stays. In the embodiment of FIGS. 1-3 and 11-12, since the frame flexes, there can be a tendency to open up the V notch of the anchoring member where the elastomeric stays are anchored. Any significant opening of the V notch can be detrimental to the integrity of the stay anchoring and cause undesirable retractor slip reducing frictional engagement of the elastomeric says or other tissue retraction member engaged therein. The geometry of the base under the V notch is designed to prevent any opening of the V notch despite the neighboring living hinge elements. Additionally, the V-notch (and any interfacing features used to anchor retractors or other instruments to the frame) are positioned within a rigid section of the frame. More specifically, as shown in FIGS. 13 and 14, the base has a thin height 210 to allow for bending. It also has a width 212 to resist torsion. The V-notch 214 has a taper (tapering inwardly in a direction toward the underlying stabilizing member) to allow progressively shorter widths the deeper the retractor is seated. The thicker material around it limits or fully restricts bending or opening of the V-notch. This V-notch structure can also advantageously be provided in the other retractor frame embodiments disclosed herein.

In the locking pin embodiment (e.g., FIGS. 4-7), this is accommodated since the v-notch or other anchor points are integral to separate, solid links that use pin hinges which limit the ability to unfavorably impact the v-notch.

Referring back to FIGS. 1A-1C, system 100 includes one or more securing apparatus to secure system 100 in a desired position relative to a particular surgical site. In some embodiments, the securing apparatus secures system 100 directly to the patient; in other embodiments, the securing apparatus secures system 100 to an intermediate layer, e.g., a surgical drape or other surface overlying skin of the patient, which in turn is secured directly and/or indirectly to the patient.

In some embodiments, the securing apparatus includes a friction fit, e.g., a rough surface that prevents movement of system 100 due to friction with the patient, a surgical drape, etc. In some embodiments, the securing apparatus utilizes gravity, e.g., system 100 is composed of sufficiently dense material that the weight of the system prevents movement relative to the patient, surgical drape, etc. when placed thereon. In other embodiments, the securing apparatus includes one or more magnets, e.g., system 100 magnetically attaches to magnets secured to the patient, a surgical drape, etc. In other embodiments, the securing apparatus includes suction, e.g., an applied vacuum holding system 100 to a patient. Note the securing apparatus can comprise a combination, i.e., one or more of, the foregoing.

In preferred embodiments, the securing apparatus includes one or more adhesive layers. This is shown in the embodiment of FIGS. 1A-1E wherein system 100 includes one or more adhesive layers 106. Adhesive layer(s) 106 are configured and include sufficient adhesive to reversibly (removably) attach system 100 to a surface, e.g., a surface of the patient's skin, surgical drapes, and the like, or combinations thereof. The adhesive layer 106 can be a continuous layer, semi-continuous layer, continuous coating, semi-continuous coating, or combinations thereof. In some embodiments, adhesive layer 106 is flexible to allow conformation to the contours of a patient's anatomy.

In some embodiments, adhesive layer 106 is positioned and configured to reversibly immobilize frame 102 relative to an incision site for surgery, e.g., proximate the midline of the patient's neck, as will be discussed in greater detail below.

The adhesive layer 106 can be positioned such that it extends outside the perimeter 102P of frame 102. The adhesive layer 106 can alternatively or additionally be positioned such that it extends inside perimeter 102P of frame 102. Thus, in some embodiments, the adhesive extends outside (laterally outwardly from) the boundary of the frame and/or inside (laterally inwardly from) the boundary of the frame so it is aligned with the interior space 1021 of the retractor 100. The adhesive layer can be separately attached to the stabilizing member or can be attached by being integral with the stabilizing member, and could extend outside or inside the periphery of the frame depending on the extent the stabilizing extends inside or outside of the frame. Note the adhesive need not extend over an entire surface of the stabilizing member such that the length and/or width of the stabilizing member could exceed the extent of adhesive coverage such that there are regions of the stabilizing member not having adhesive or an adhesive layer secured adhered thereto.

In some embodiments, adhesive layer 106 is integrated with frame 102; in other embodiments, adhesive layer 106 is integrated with second surface 102S" of frame 102. In some embodiments, adhesive layer 106 includes one or more biocompatible adhesives.

The adhesive layer 106 reversibly adheres to skin, e.g., of a human patient, and in some embodiments, adhesive layer 106 could maintain sufficient adhesion to allow for multiple uses, i.e., the frame is positioned and then can be repositioned at least once with system 102 still being useful for its intended purpose.

The adhesive layer 106 can in some embodiments include a removable protective layer (not pictured) configured to protect adhesive layer 106 until such time that it is desired for the adhesive layer to interface with a surface, e.g., a patient, surgical drapes, etc. FIG. 18 shows one such protective layer that can be utilized.

Figure 18A:
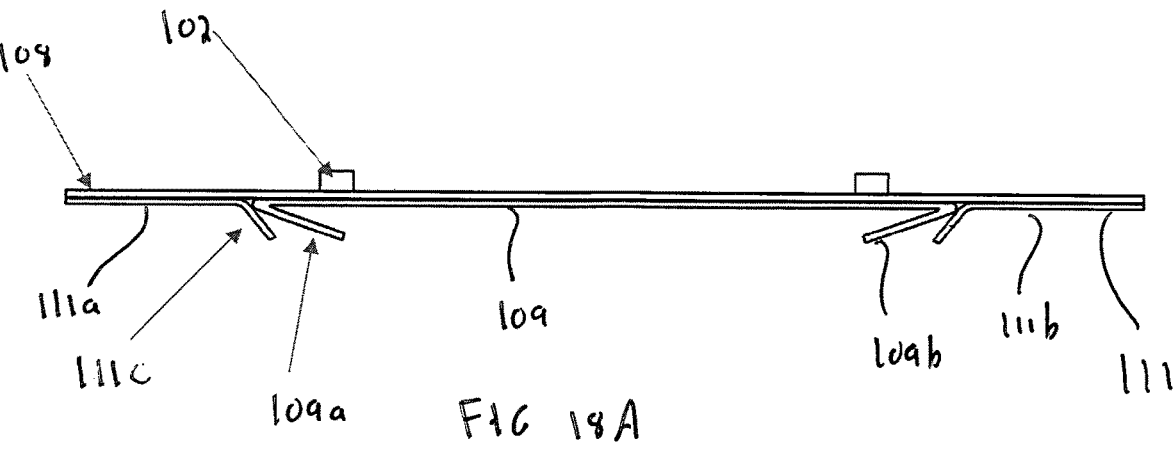
Figure 18B:
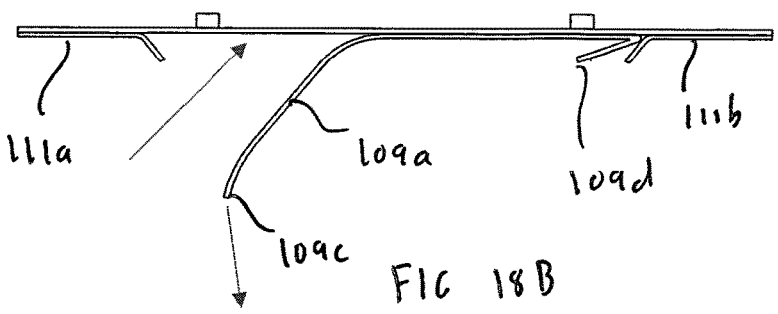
Figure 18C:
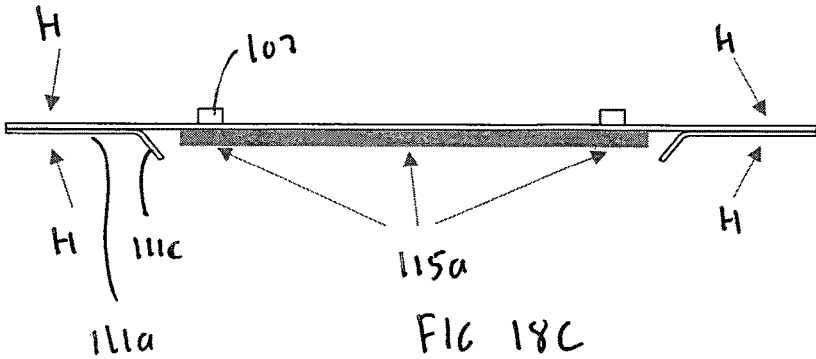
Figure 18D:
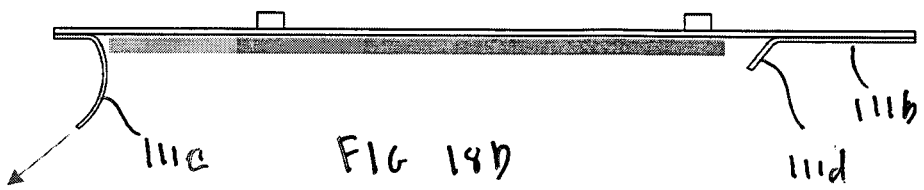

FIGS. 18A-18C illustrate one embodiment of a multiple adhesive protective layer. With initial reference to FIG. 18A, protecting the adhesive layer on the bottom surface of the stability member 108 of the device is a first peel away layer 109 and second peel away layer 111. Peel away layer 109 has a tab 109a and 109b on each side for grasping by the user to remove the layer 109. Outward of peel away layer 109 is a second peel away layer 111 have a side 111a and a side 111b.

In use, with reference to FIGS. 18B-18E, the first peel away layer 109 is removed by pulling on tab 109c of side 109a and/or tab 109d of side 109b of peel layer 109 as shown in FIG. 18B to remove the first layer 109. This exposes the adhesive surface 115a as shown in FIG. 18C.

Figure 18E:
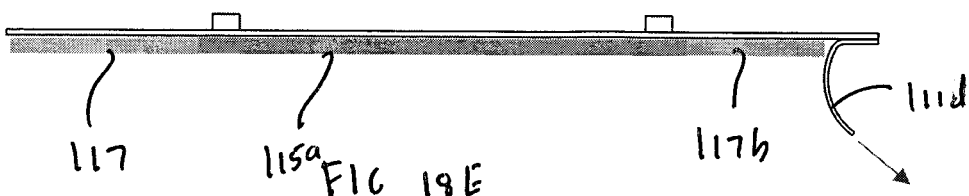
Figure 18F:
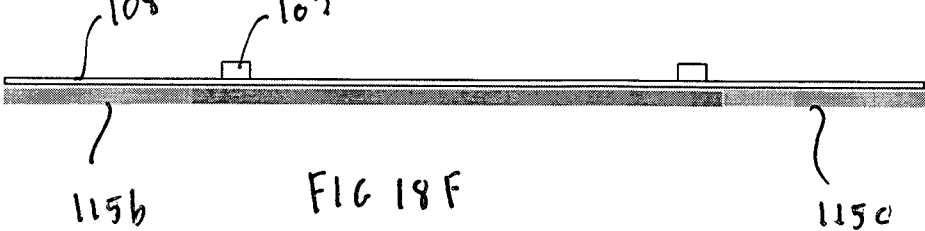

Second peel away layer 111 still remains on the device to protect adhesive layer portions 115b, 115c while adhesive layer portion 115 is exposed. The device is held by the user at the protected sides (FIG. 18C) as shown by the arrows H on both sides of the stability member 108, and placed on the operative site. The adhesive surface 115a now adheres to the patient's skin or surgical drape. Next, the second peel away layer 111 is removed by grasping tab 111c of layer 111 to expose adhesive layer 115b and adhesive layer 115b is adhered to the patient's skin or drape (FIG. 18E). Then, the tab 111d is pulled to remove portion 111b of second peel away layer 111 to expose adhesive surface 115c which is adhered to the patient's skin or drape as shown in FIG. 18F. As shown, the entire adhesive surface/layer 115 (regions 115a, 115b and 115c) (or alternatively a majority of the adhesive surface/layer 115) is now in adhesive contact with the patient's skin or drape.

Note that the double protective layer of FIGS. 18A-18E can be utilized with the other retractor systems disclosed herein as well as with other retractor systems.

Referring again to FIGS. 1A-lE, system 100 includes at least one stabilizing member 108 secured to the retractor frame. In some embodiments, the one or more of stabilizing members 108 are of sufficient thickness and/or suitable materials to resist bending. In some embodiments, the one or more of stabilizing members 108 are flexible. The one or more of stabilizing members 108 can be positioned outside perimeter 102P of frame 102 so they extend outwardly from frame 102, positioned inside perimeter 102P of frame 102 so they extend inwardly from frame 102, or positioned both inside and outside the frame 102P. In some embodiments, stabilizing members 108 are positioned proximate one or more boundaries of an adhesive layer 106. The stabilizing members 108 can in some embodiments have a thickness between about 30 μm and about 0.5 cm. In some embodiments, stabilizing members 108 can have a thickness between about 30 μm and about 1 mm. In some embodiments, stabilizing members 108 have a thickness between about 30 μm and about 100 μm. Other thicknesses are also contemplated. In some embodiments, the thickness of one or more of the stabilizing members 108 is variable along at least one axis thereof, as will be discussed in greater detail below.

In some embodiments, one or more stabilizing members 108 are attached to frame 102 by being integrated with frame 102.

In the embodiment of FIGS. 1A-1E, the stabilizing members 108 include one or more features 108R having a body having a length and width. Feature 108R includes an elongated body having a width generally greater than a length, but alternatively can have a length greater than a width or alternatively equal to the width. Feature 108R includes one or more continuous surfaces. Feature 108R, in some embodiments, can include one or more stiffening features such as one or more rib features that allow for bending along the axis of the rib but resist compressive and tensile forces. In some embodiments, feature 108R has a generally lattice-shaped construction. In some embodiments, feature 108R includes elongated sections having a generally lattice-shaped construction. The lattice construction allows for bending in the plane perpendicular to the frame, but maintains composure in both compressive and tensile loading forces. That is, the design of the lattice allows for more bending at the distal end where compressive and tensile loads are smaller and less bending at the proximal end where compressive loads are higher due to the additive affect of the proximal portion of the stabilizing member, i.e., ribs that allow bending along the axis but resist compressive and tensile forces. Feature 108R can have for example a thickness between about 100 μm and about 0.5 cm, although other thicknesses are also contemplated. The embodiment shown in FIG. 1A portrays a system 100 including 8 features 108R, however the present disclosure is not intended to be limited in this regard, as any number of stabilizing members 108 can be employed to help stabilize system 100 when positioned on a surface such as proximate an incision site, e.g., the embodiments of FIGS. 1B and 1C include five features 108R. In some embodiments, one or more features 108R are positioned outside perimeter 102P of frame 102; in other embodiments, one or more features 108R are positioned inside perimeter 102P of frame 102 and in other embodiments, one or more features 108R are positioned both outside (extend outwardly from) and inside (extend inwardly from) perimeter 102P of frame 102. The one or more features 108R can be attached to frame 102 as a separate attachment or attached via integration with frame 102.

In some embodiments, the one or more stabilizing members 108 include one or more sheets 108S. Sheets 108S have a length and a width defining a surface area thereof, the sheet being flexible to conform to the corresponding surface area of a surface, e.g., proximate and/or covering an incision site on a patient. The embodiments shown in the figures portray a system 100 including generally rectangularly shaped sheets 108S, however the present disclosure is not intended to be limited in this regard, as sheets 108S of different configurations and different sizes (length, width and/or thickness) than that shown in FIG. 1C can be suitable to help stabilize system 100 when positioned on a surface such as proximate an incision site and provide tensile and compressive load resistance, as will be discussed in greater detail below. In some embodiments, sheet 108S is formed of a suitable biocompatible material that is sufficiently flexible to conform to a patient's anatomy. The sheet 108S can be formed from one or more polymers for example. The one or more sheets 108S can be positioned outside (extend outwardly from) perimeter 102P of frame 102 or alternatively in or in addition positioned inside (extend inwardly from) perimeter 102P of frame 102. In some embodiments, one or more sheets 108S cover the majority of an interior space 102I defined by perimeter 102P, and in other embodiments, cover a minority or an entirety of an interior space 102I defined by perimeter 102, e.g., is an incise drape. The one or more sheets 108S can be integrated with frame 102 or separately attached thereto.

The sheet(s) 108S can include one or more antimicrobial agents embedded or applied thereon. In some embodiments, the sheet(s) 108S are configured to be cuttable via a surgical tool, e.g., whereby sheet 108S is an incise drape and is configured to be cuttable with a scalpel, thus composed of an incisable material.

The system 100 can include a single stabilizing member 108 as an alternative to multiple stabilizing members 108. The single stabilizing member 108 can in some embodiments be attached to the frame by being integrated with frame 102 or attached as a separate component to the frame. Alternatively, in some embodiments, a single stabilizing member extends outwardly from frame 102 and inwardly from frame 102 or alternatively attached as a separate component to the frame. In some embodiments, the system 100 can include a single feature 108R. In some embodiments, system 100 includes a single sheet 108S. In some embodiments, system 100 includes a single feature 108R and a single sheet 108S. In alternate embodiments, system 100 includes a plurality of features 108R and/or a plurality of sheets 108S.

Figures 2A, 2B, 2C:
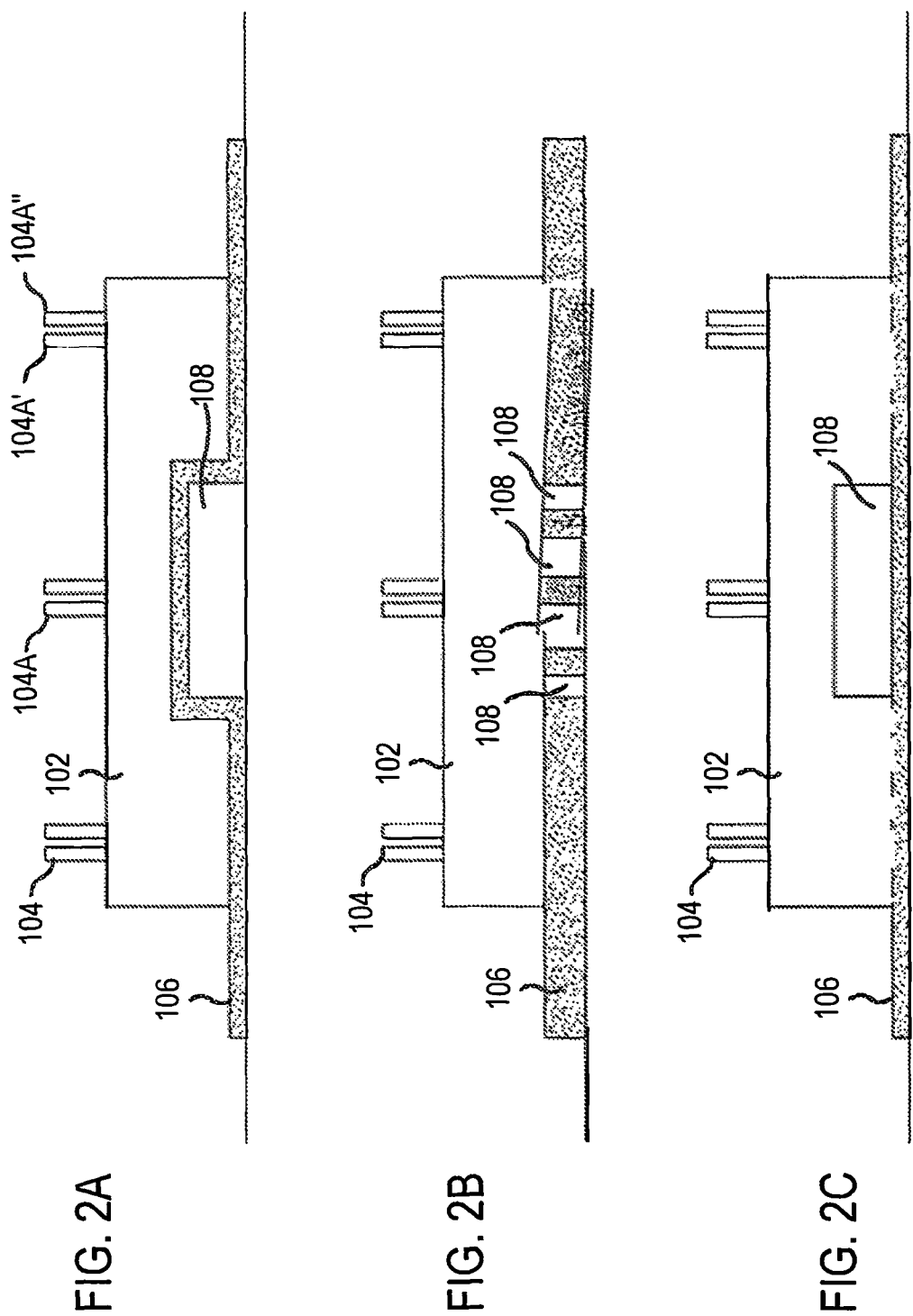
FIG. 2A is a side schematic view of an embodiment of the system of the present invention having one or more stabilizing members integrated into the adhesive layer.
FIG. 2B is a side schematic view of an embodiment of the system of the present invention having one or more stabilizing members positioned under an adhesive layer.
FIG. 2C is a side schematic view of an embodiment of the system of the present invention having one or more stabilizing members on an adhesive layer.
Figure 2D:
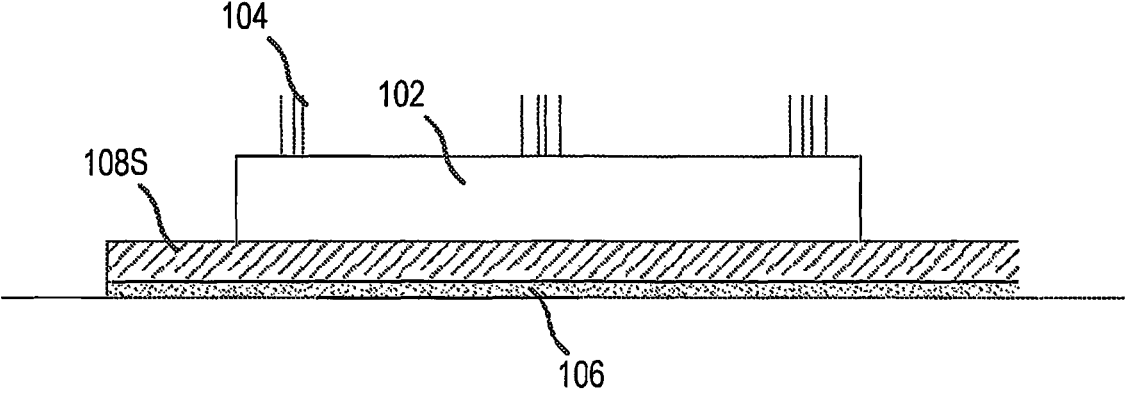
FIG. 2D is a side schematic view of an embodiment of the system of the present invention having one or more sheets positioned on an adhesive layer.

Referring now to the embodiments of FIGS. 2A-2H, the stabilizing members 108 have an adhesive layer 106. In the embodiment of FIG. 2A, the stabilizing members 108 are positioned under the adhesive layer 106; in the embodiment of FIG. 2B, the stabilizing members are positioned in (i.e., integrated in) adhesive layer 106; and in the embodiment of FIG. 2C, the stabilizing members are positioned on (on top of) adhesive layer 106. The adhesive layer 106 can cover an entire surface of a stabilizing member 108 or cover only a portion (i.e., less than the entire surface) of stabilizing member 108. Referring specifically to FIG. 2D, in embodiments of system 100 with one or more sheets 108S, the sheets are positioned on an adhesive layer 106. In some embodiments, system 100 includes one or more features 108R and one or more the sheets 108S. In some embodiments, one or more features 108R are positioned on a sheet 108S, under a sheet 108S, or in a sheet 108S, or combination thereof. Note the term "adhesive layer" encompasses a separate layer of adhesive attached to the stabilizing member; however, it should be understood that the stabilizing member could itself have an adhesive surface which can be considered an adhesive layer. In either case, the stabilizing member adhesively adheres to the skin or surface, e.g., surgical drape.

Figures 2E, 2F, 2G:
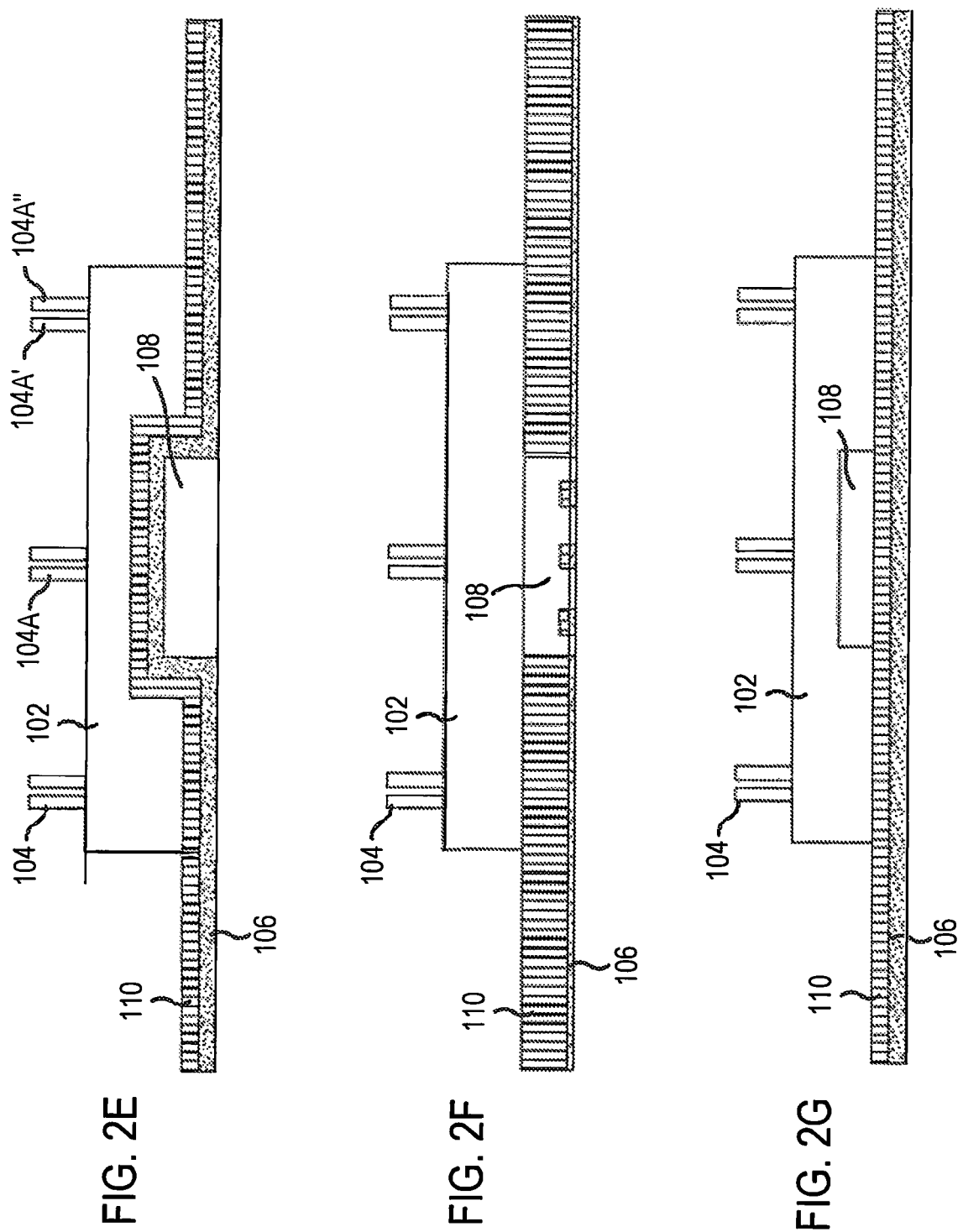
FIG. 2E is a side schematic view of an embodiment of the system of the present invention having an adhesive layer positioned on the stabilizing member.
FIG. 2F is a side schematic view of an embodiment of the system of the present invention having an adhesive layer integrated in the stabilizing member.
FIG. 2G is a side schematic view of an embodiment of the system of the present invention having an adhesive layer positioned under the stabilizing member.
Figure 3:
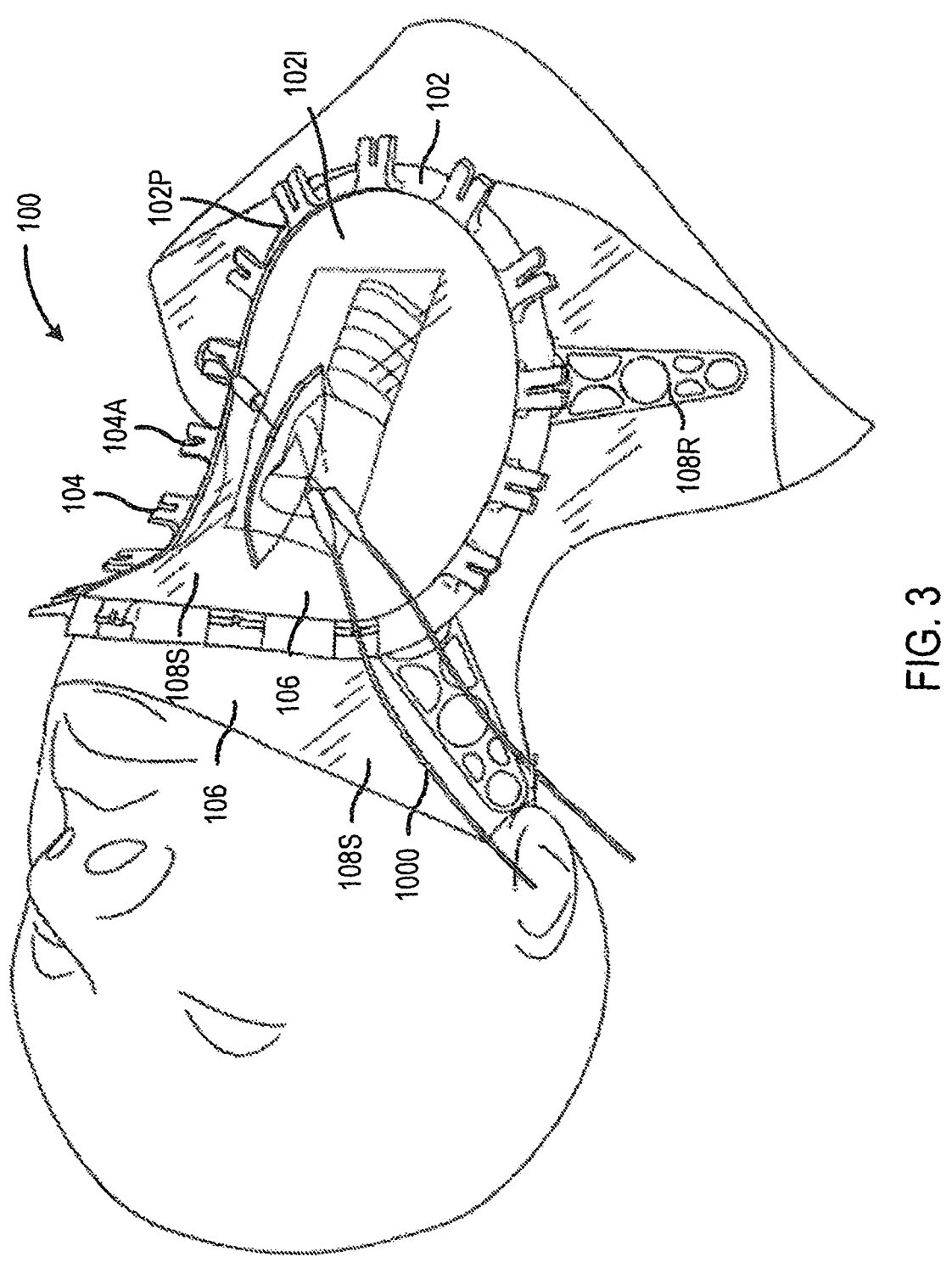
FIG. 3 is a perspective view of an embodiment of the retractor system of the present invention shown in use on a neck area of a patient.

FIGS. 2E-2G illustrate embodiments similar to FIGS. 2A-2C except with the provision of surgical drape 110. This is discussed in detail below.

The stabilizing members can use varying thickness and geometry to control tensile/compressive loading forces and ability to conform to various geometries. For example, a thinner stabilizing member (membrane), such as polyurethane of 0.03 mm by way of example, permits high bending and conformity but low compressive strength. This is better suited where retractor loading is minimal but patient anatomy is complex, such as retraction of the rectus muscles during ocular surgery. A thicker membrane, e.g., about 1.0 mm in thickness, permits some bending but have higher compressive and tensile strength. This is better suited for applications where retractor loading is moderate but patient anatomy is not flat, e.g., retraction of soft tissue during anterior neck dissection as shown in FIG. 3. A still thicker membrane, e.g., polyetheretherketone about 50 mm in thickness, permits little or no bending but maximal compressive and tensile strength. This is better suited for applications where retractor loading is very high but patient anatomy is relatively flat, e.g., retraction of paraspinal muscle elevation during posterior laminectomy and the system is applied to the back with minimal curvature. Note these thicknesses are provided by way of example as other thicknesses are also contemplated to suit the clinical applications.

Referring now to FIG. 3, system 100 described above is shown in use. The system 100 is positioned on the patient's anatomy such that frame 102 is proximate an incision site. The system 100 is configured to resist and distribute tensile and compressive loads even while subjected to a bend radius of less than 45 mm. FIG. 3 portrays a system 100 in use for surgery on a patient's neck by way of example, it should be appreciated that the present disclosure is not intended to be limited in this regard, as system 100 can be designed for use in a variety of surgical locations such as the neck (more flexible frame 102 and stabilizing members 108, bend radius between about 45 mm and about 125 mm), the spine (more rigid frame 102 and stabilizing members 108, bend radius greater than about 125 mm), the eye, (thinner frame 102 and/or stabilizing members, bend radius less than about 45 mm), etc.

In the embodiment of FIG. 3, sheet 108S covers the area within perimeter 102P of frame 102, as well as an area surrounding perimeter 102P. Thus, when in use, the surgeon intuitively places an incision through sheet 108S, e.g., an incise drape, near the middle of frame 102. Rigid or elastic band retractors 1000 can then be attached to anchor points 104 on frame 102 to retract tissue. Stabilizing members 108, i.e., features 108R and sheet 108S, integral with frame 102, act to hold system 100 in place.

As discussed above, frame 102 is configured to conform along an axis that is substantially parallel to the surface of the substrate, without allowing excessive flexion in an axis substantially perpendicular to the device. Adhesive layer 106 holds system 100 in place, affixing frame 102 and stabilizing members 108 such that the system sits relatively flush with the patient's anatomy. This allows for interoperative repositioning of the patient while maintaining strength sufficient to resist loads, e.g., from retractors 100A. Further, system 100 distributes loads applied from attached devices/tools, e.g., retractors 1000, throughout frame 102 and stabilizing members 108 to the substrate to which the system is attached, i.e., patient's skin or surgical drape. Stabilizing members 108 are configured to provide tensile and compressive load resistance, distributing those loads over a larger area and reducing the loads felt by adhesive layers 106. This allows increased performance and ease of handling of adhesive layer 106, while also allowing the adhesive layer to conform to patient-specific anatomy. The coverage area of adhesive layers 106 and stabilizing members 108 contribute to the ability of system 100 to maintain position on the desired surface. As frame 102 is integrated with stabilizing members 108 which in turn have a large surface area, the loads applied are distributed over an expansive domain and this results in a very low risk of detachment or movement and, as a result, a high degree of security. By integrating a stabilizing member 108 with an adhesive layer 106 applied to the surface of patient's anatomy, motion of the adhesive layer is prevented, even on uneven surfaces with application of non-directional retraction forces applied to system 100. Stabilizing sheet 108S may remain anchored to the surface of the operative site whilst allowing flexible frame 102 to deform when the patient's anatomy is repositioned without becoming detached from the operative site. Previous solutions would require repositioning with at least two hands, thereby extending length of surgery and complications.

Features 108R and sheets 108S also add resistance to the retractor holders that are anchored to frame 102. Due to stabilizing members 108 extending into and beyond perimeter 102P, forces applied to frame 102 by retractors 1000 affixed thereto are counteracted, thus stabilizing system 100 even when the forces applied by the retractors attached to the frame are otherwise unbalanced. The continuous frame 102 distributes these forces through a broader area of sheet 108S and/or features 108R, whereas a disconnected frame segment would have a much smaller area of sheet experiencing tensile loading. Through utilizing a large surface, compliant frame 102 can translate the loads placed by retractors 1000 from a single point on the device, throughout the frame and then distributed to other areas of sheet 108S that would not otherwise be loaded. This allows for much more efficient immobilization than if frame 102 was only stabilized by a smaller segment of sheet 108S or adhesive layer 106 just under the frame itself. The enlarged surface area of the attachment site increases the stability in the whole device so that retraction forces are easily balanced, even when retraction is mono-directional. In some embodiments, features 108R and sheet 108S are shaped in a way that anticipates retractor loading to maximize the amount of integral sheet that is in tension.

As discussed above, control of loading forces to system 100 is performed via design and optimization of at least one or more of the composition, thickness, and geometry of stabilizing members 108. The thickness affects the flexibility, as thinner stabilizing members provide higher flexibility and thinner stabilizing members provide greater flexibility. Materials utilized can also affect flexibility.

Further, as discussed above, in some embodiments, stabilizing members 108 can have a variable thickness, i.e., the thickness of the stabilizing members is not consistent throughout the member. For example, feature 108R might be thicker at a proximal end (closer to the frame periphery) than at a distal end (further outward from the frame periphery), allowing for more compressive resistance at the proximal end (with less flexibility), but more flexibility at the distal end (with less compressive resistance when considering additive loading). Finally, in some embodiments, the geometry of stabilizing member 108 can be configured to more effectively distribute loading forces, e.g., by having a plurality of bending radii capabilities and associated compressive/tensile loading resistance capabilities. In some embodiments, stabilizing members 108 include a plurality of ribs that allow bending in the plane substantially perpendicular to frame 102 while still maintaining tensile compressive loading. In some embodiments, the geometry of stabilizing members 108 allows for more bending at the distal end thereof (where compressive and tensile loads are smaller) and less bending at the proximal end thereof (where compressive loads are higher due to the additive effect of the proximal portion of the stabilizing member). Thus, geometry and/or thickness changes can provide for regions of varying flexibility and varying compressive resistance of the stabilizing member.

In some embodiments, a protective layer is provided over adhesive layers 106 to protect the adhesive until it is time to position system 100. The protective layer is removed to allow exposure of adhesive layer(s) 106. In some embodiments, adhesive layers 106 are exposed immediately prior to placement by the surgeon or surgical assistant and applied to the surface of contact.

In the embodiment of FIG. 18A, as discussed above, the cover for the adhesive includes two peel away layers.

In some embodiments, system 100 further includes one or more straps (not pictured), that secure frame 102 to the patient e.g., around the neck, leg, back, etc., or another anchor point. In some embodiments, system 100 includes further includes one or more clamps (not pictured), e.g., clamping the frame to the patient, a bedframe, or other rigid structure.

The adhesive layer can be adhered to the frame by various methods such as superglue, double sided tape, welding or mechanical methods of attachment.

Referring back to FIGS. 1C and 1E, in some embodiments, system 100 includes a surgical drape 110 integrated with frame 102, integrated with one or more of stabilizing members 108, or combinations thereof. Surgical drape 110 is configured to provide a barrier between the surface upon which system 100 is applied, and a surrounding environment. In some embodiments, surgical drape 110 is positioned and configured to cover an incision site. In some embodiments, surgical drape 110 is configured to be cuttable (incisable) via a surgical tool, e.g., a scalpel. The surgical drape 110 can be positioned (extends laterally outwardly) from outside perimeter 102P of frame 102, positioned inside (extends laterally inwardly) of perimeter 102P of frame 102 or positioned both outside and inside perimeter 102P of frame 102.

Figure 2H:
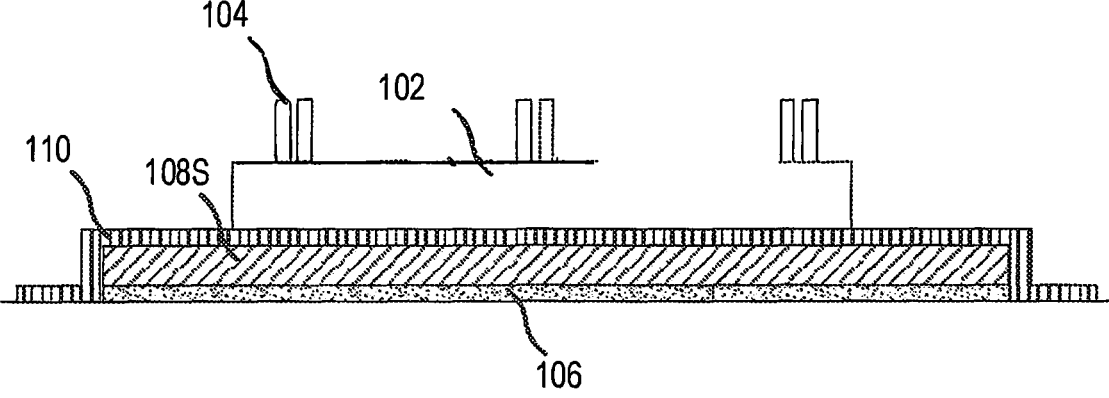
FIG. 2H is a side schematic view of an embodiment of the system of the present invention having one or more adhesive layers integrated with one or more stabilizing members.

Referring to FIGS. 2E-2H, in some embodiments, surgical drape 110 is integrated with an adhesive layer 106. In some embodiments, surgical drape 110 is positioned on stabilizing member 108 (see FIG. 2E), positioned or integrated in stabilizing member 108 (see FIG. 2F), or positioned under stabilizing member 108 (see FIG. 2G), or combinations thereof. Referring specifically to FIG. 2H, in embodiments of system 100 with one or more sheets 108S, surgical drape 110 can be integrated with a sheet 108S or alternatively positioned above under sheets 108S. In some embodiments, surgical drape 110 is coextensive with a stabilizing member 108*d*; in other embodiments, surgical drape 110 has a larger surface area, i.e., a greater length and/or width, than the stabilizing members 108 so it extends laterally beyond one or more of the edges of the stabilizing member. In other embodiments, it has a smaller surface area than stabilizing members 108. Surgical drape 110 can be attached to frame 102, stabilizing members 108, the patient, etc. via adhesive, magnets, hook and loop fasteners, or combinations thereof. In some embodiments, surgical drape 110 includes one or more antimicrobial agents.

Thus, the surgical drape can be a separate layer or can be integral with the stabilizing member. In some embodiments, the stabilizing member itself can form the surgical drape to provide a sterile barrier to protect the patient.

Figures 8, 9:
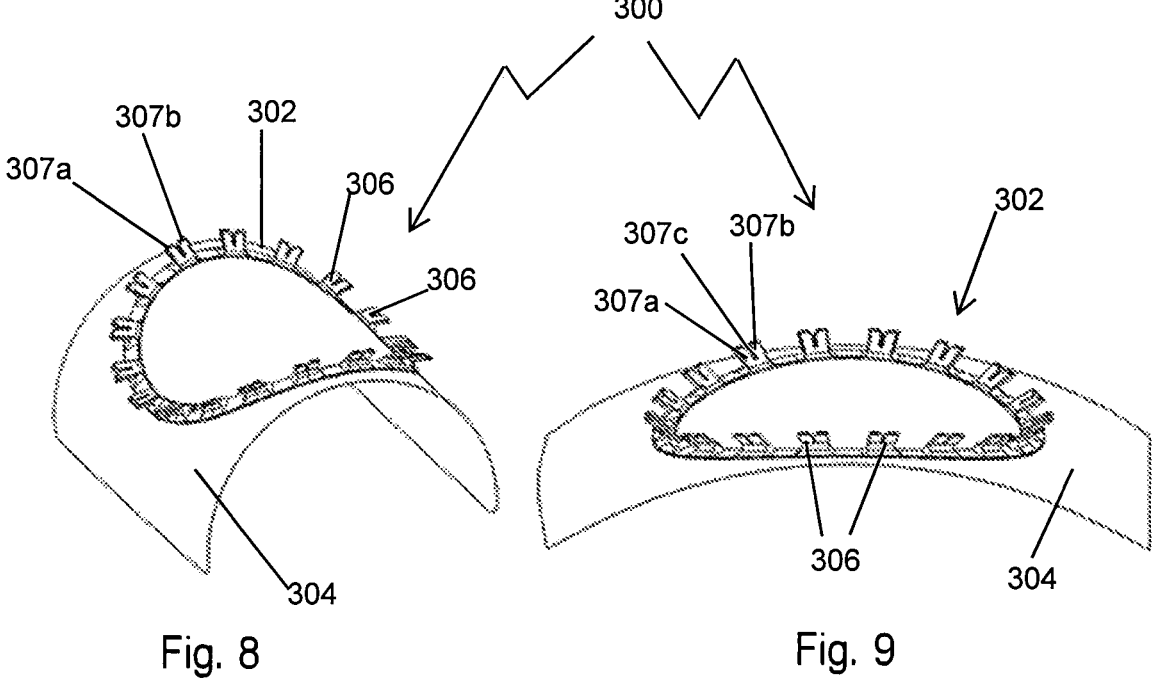
FIGS. 8 and 9 show a frame of an embodiment of the present invention conforming to a patient's anatomy.
Figure 10:
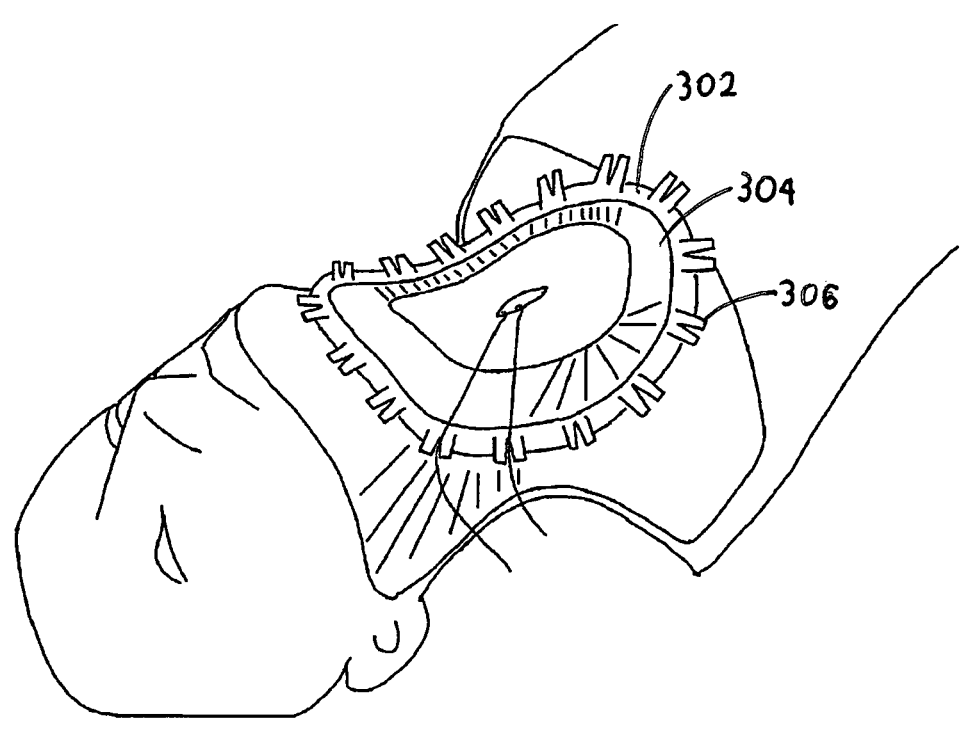
FIG. 10 shows a system of an embodiment of the present invention in use on a neck area of the patient and showing distribution of loads applied from the device throughout the frame and stabilizing member.
Figures 11, 12:
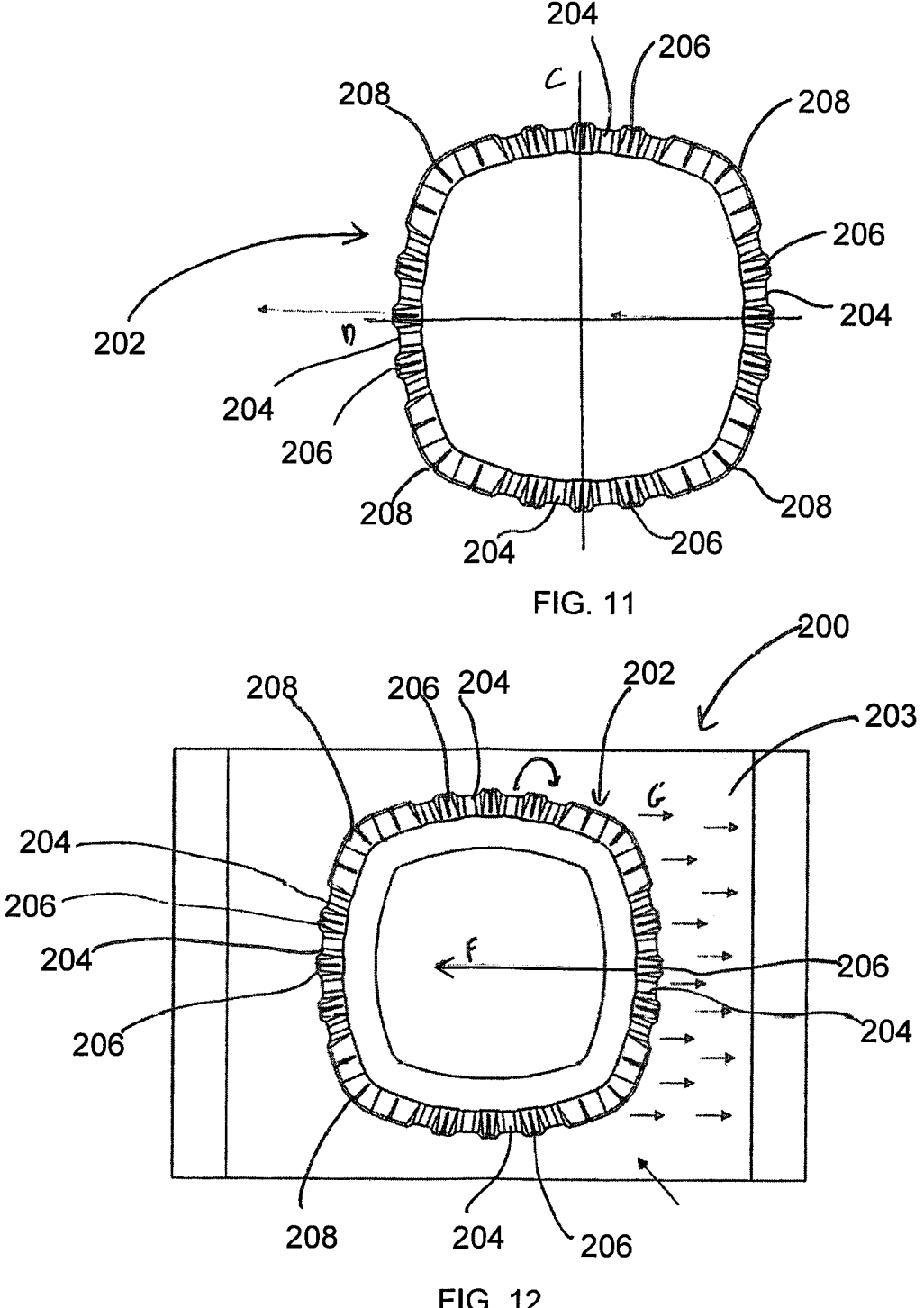
FIG. 11 is a top view of an alternate embodiment of the retractor frame of the present invention, the frame shown without a stabilizing member to illustrate movement of the frame upon application of unilateral retraction.
FIG. 12 is a top view similar to FIG. 11 showing the retractor frame with a stabilizing member attached thereto to resist loads upon application of unilateral retraction.

FIGS. 8-10 show an alternate embodiment of the present disclosure. With reference to FIGS. 8 and 9, the retractor is designated generally by reference numeral 300 and has a stabilizing member 304 attached to a frame 302 configured to conform to a patient's specific anatomy, e.g., a surface of the patient's skin, surgical drapes, and the like, or combinations thereof. The frame can be constructed out of one or more flexible materials, e.g., nylon. In some embodiments, the frame 302 is constructed out of one or more malleable or flexible materials, e.g., 304 annealed stainless steel. In some embodiments, the frame 302 is constructed out of at least one flexible material and at least one malleable material.

The stabilizing member 304 can be of the form discussed herein and can in preferred embodiments adhesively secure the device 300 to the patient's skin or drape overlying the patient. Since the stabilizing member 304 can be the same as the stabilizing members discussed herein, including their alternatives, for brevity, the stabilizing member configuration and function is not repeated herein. Therefore, it should be understood that the configurations, functions, and alternatives discussed herein are fully applicable to stabilizing member 304. Similarly, retractor 300 can also include a surgical drape such as that discussed above for system 100.

The frame, in some embodiments, can include at least one coating layer, e.g., a soft rubberized material for better comfort and integration with a membrane. Such coating layer can be utilized with any of the frames disclosed herein.

The frame 302 includes at least one anchoring member 306 (also referred to herein as an anchor point). As shown, the frame 302 includes multiple anchor points which can be rigid or elastic or flexible. All of the anchoring members 306 can be flexible, all can be rigid or some can be flexible and some rigid. For clarity, only a few of the anchoring members 306 are labeled. These anchor members (points) enable the attachment of various tools, e.g., rigid retractor arms, elastic band retractors (such as the Lonestar Stays), other instrument attachments, or combinations thereof, while enabling a clear view during surgery, i.e., limiting obstruction of the surgical field. The anchor points 306 can be of any suitable shape so long as they are able to maintain the position of tools attached to the frame in a desired location, e.g., relative to a surgical site. In some embodiments, the tool is maintained in position by a friction fit with one or more anchor points 306, by mechanical locking, e.g., bayonet, etc., or combinations thereof. In some embodiments, the anchors include a plurality of prongs or fingers 307*a*, 307*b*, having a groove or notch 307*c* formed between the prongs 307*a*, 307*b*, between which tools can be held by frictional fit within the groove or notch to maintain their position relative to the desired location. The notches in some embodiments are tapering v-notches as in the embodiment of FIG. 13, however other shaped notches are also contemplated. The prongs can be positioned at an obtuse angle with respect to the periphery of the frame (angled outwardly away from the center of the frame) as shown in FIG. 9.

The frame 302 is designed to conform to extreme patient anatomy. The frame is designed to conform to the patient's anatomy while providing sufficient stability for tissue retraction at the anchor points 306. The frame is designed to allow deformation in the plane perpendicular to the surface of the anatomy but resist deformation in the plane parallel to the surface of the anatomy. The frame is shown as a ring shaped but other shapes such as ovular or U-shaped, e.g., shaped as segment of ring, oval, etc. can alternatively be utilized.

As shown in FIG. 10, the system distributes loads applied from attached devices/tools throughout the frame 302 and the stabilizing member 304 to the substrate the system is attached to, i.e., patient's skin or surgical drape. The stabilizing member is shown in the form of a membrane which is in the form of an adhesive film. The image indicates a broad area of coverage provided by the protective membrane 304 and the areas of membrane 304 expected to be experiencing tensile loading, thereby reinforcing the position of the elastic retractors which are attached to the anchoring members 306 of the frame 302 (areas of presumptive tensile loading with vector lines in black). As the frame 302 is integral to the membrane 304 which in turn has a large surface area, the loads applied are distributed over an expansive domain and this results in a very low risk of detachment or movement and, as a result, a high degree of security. The membrane 304 may remain anchored to the surface of the operative site whilst allowing the flexible frame 302 to deform when the patient's anatomy is repositioned without becoming detached from the operative site. Previous solutions would require repositioning with at least two hands, thereby extending length of surgery and complications.

The membrane 302 also adds resistance to the retractor holders that are anchored to the frame 302 at anchoring members or points 306. The image indicates the area of membrane 304 that is resisting the loads of the elastic retractors. The continuous frame 302 distributes these loads through a broader area of the protective membrane 304, whereas a disconnected frame segment has a much smaller area of protective membrane experiencing tensile loading (areas of presumptive tensile loading with vector lines in black). The displacement of the disconnected segment supports the finding that an integrated retractor membrane is substantially stronger. Through utilizing a large surface area as is available with membrane attachment, the compliant frame can translate the loads placed by retractors from a single point on the device, throughout the frame and then distributed to other areas of the integral membrane that would not otherwise be loaded, something not possible in a disconnected frame. This allows for much more efficient immobilization than if the frame was only stabilized by a smaller segment of integral membrane or just under the frame itself. The enlarged surface area of the attachment site increases the stability in the whole device so that retraction forces are easily balanced, even when retraction is mono-directional. In some embodiments, the integral membrane may be shaped in a way that anticipates retractor loading to maximize the amount of integral membrane that is in tension.

It should be appreciated that the discussion above regarding load distribution, balance of forces, more efficient immobilization of the frame 302 and membrane 304 is fully applicable to the other frame/membrane (stabilizing member) embodiments of FIGS. 1-7 and 11-18A disclosed herein.

The systems of the present invention are also designed so there are no concentrated forces on a small area of the skin or collapse of the retractor which could cause compression of arteries, e.g., compression of carotid arteries.

The frames disclosed herein are optimized in anatomical flexibility and strength by incorporation of the membrane, i.e., adhesive film, attachment to the skin of the patient or to a drape that has been applied. Thus, the adhesive film provides the preferred approach.

To provide sufficient stability for the frame, the adhesive film is pliable enough so that it sufficiently contacts the variable surface geometry of the skin or drape. Second, it has sufficient adhesion to both the skin and drape and skin, without being overly adhesive that would result in injury to the patient and damage the patient's skin during removal for repositioning or at the end of the surgical procedure.

The use of the adhesive film of the present invention provides auxiliary strength to the system by translating the retraction loads through the frame to the adhesive film membrane. The adhesive film can then distribute the retraction loads over a broad area determined by the size and position of the adhesive sheet. By spreading these loads over a broad area, any high stresses that may be translated to the patient can be minimized. Through analytical and empirical evaluations, the inventors determined that the optimal area of the adhesive film beyond (outward of) the perimeter of the frame is between about 40% and about 90% of the area within the perimeter of the frame. The optimal area for the adhesive laying within the perimeter of the frame is between about 22% and about 60% of the area within the perimeter of the frame. It should be understood that these percentages provide for optimization of the retractor, however, it is envisioned that other percentages can also be utilized if sufficient to enable use of the retractor as disclosed herein.

The location of the adhesive film is relevant relative to the retraction force vectors that are applied by the elastic stays. When the retraction loads are not balanced through the frame, residual loading can be accommodated by the shear and peel strength of the adhesive bond to the patient's skin or drape. In one example, adhesive properties of the film which have 90 degree Peel Adhesion on PE of 5N/in, Finat Tack of 47N/in, moisture vapor transition rate of 385 g/m²/ 24 hrs, and a 90 degree release of 41 g/2 in have proven beneficial, although moderate variations in those properties will provide similar function. These properties allow achievement of optimal performance of between x and y in shear on a flat plane (Ref ASTM standard) and between x and y in peel strength (Ref ASTM standard).

An additional benefit of the adhesive film is that is can be used to keep the frame in a conformal, low-profile position despite the tendency of the frame to return to its relatively flat manufactured state. This residual springback loading can be accommodated by the adhesive film. In an exemplary embodiment, the adhesive film forms a web within the perimeter of the frame that is between 22% and 60% of the area within the perimeter of the frame. This helps to combat peel failure that would be more likely if the film ended at the inner periphery. It is also beneficial to optimize the area of the film (membrane/stabilizing member) resistant to retractor load. This area is a function in part of the total area (length and width) of the film.

When applied to drapes, however, the loads are translated first to the drape through the adhesive film, and then to the patient, resulting in drape creep ($C_{drape}$). Drape creep is defined as the drape moving over the patient's anatomy when loads are being tied to it. This is commonly experienced when elastomeric stays are clamped with hemostats directly to the drapes themselves, resulting in delay in the procedure as the surgery is routinely paused while the stays are repositioned. Testing indicates that the aforementioned configuration is prone to the same failure mode, but unlike utilizing hemostats an adhesive patch would not be a viable candidate for multiple repositioning during a procedure. This can be understood with reference to FIG. 15A.

Figure 15A:
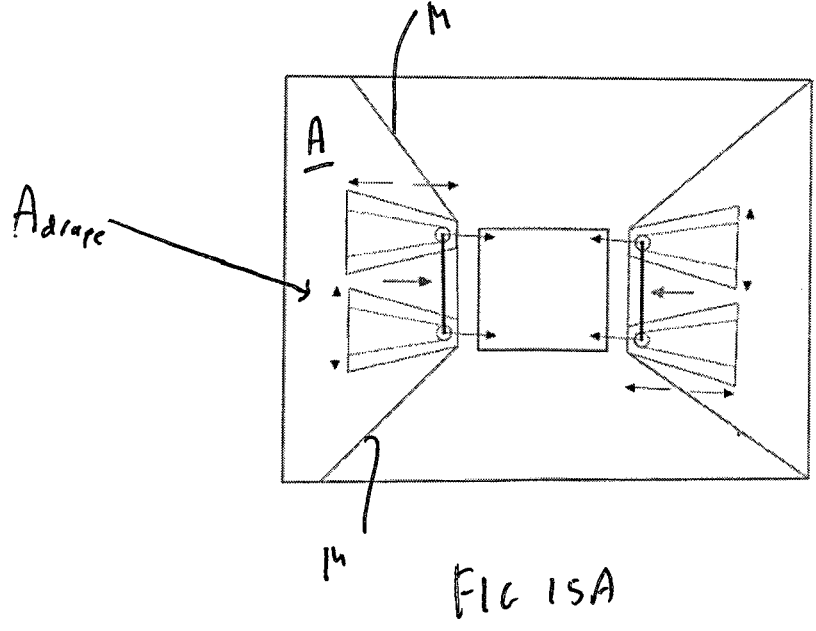
FIGS. 15A-15E illustrate how the retractor of FIG. 11 reduces drape creep.
Figure 15B:
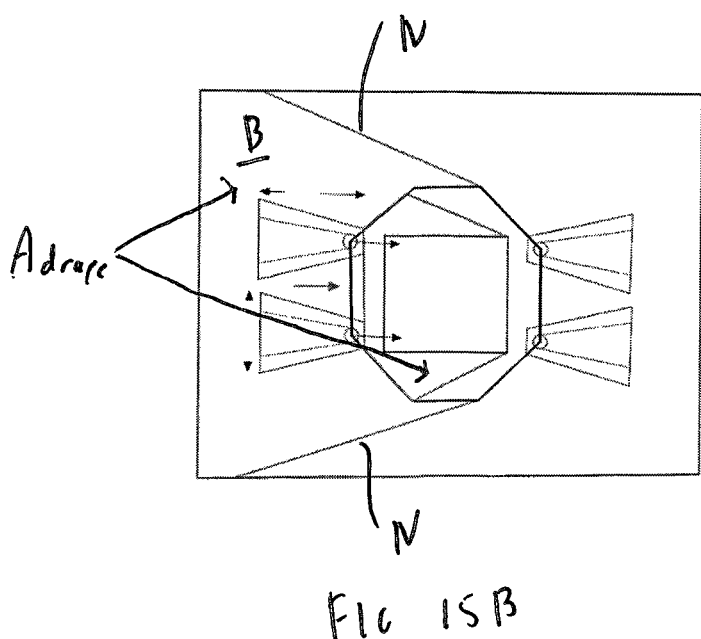

The area of the drape under load is represented by the area within the boundary defined by lines M (area A to the left of the lines M as seen in the schematic view of FIG. 15A).

The frame system of the present invention addresses drape creep by connecting retractor points in a semi rigid pattern, shown as a closed loop below (although a disconnected frame could also be utilized). This allows for two things. First, drape creep is minimized as the connecting members all contribute to resisting unilateral drape creep by maximizing the area of the drape under load $A_{drape}$. Secondly, by resisting on the contralateral side of the loop which the drape itself is typically less prone to creep as it is taped to the patient's skin and thus increases the friction coefficient $Fr_{drape}$. Thirdly, by applying the load to the drape throughout the entire portion of the area of the film that is resistant to retractor load $F_{film}$, achievable by translating the loads through the frame. The resulting $F_{film}$ applies the resultant load from the retractor, $F_{ret}$, over a larger surface area, which overcomes the friction coefficient of the drape. This area is designated by area B in the schematic view of FIG. 15B within the boundary of lines N which as can be seen includes an area inside the frame and is larger than the area A of FIG. 15A.

Figure 15C:
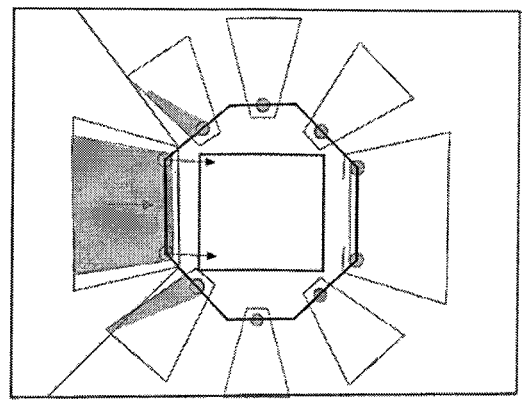

It should be noted that the above approach is under unilateral loading to illustrate the extreme end of drape creep. However, by incorporating the multiple stiff members in a loop it becomes possible to anchor retractors along the entire periphery of the frame. To maximize the stability as explained above, adhesive films are placed around the periphery as shown in the schematic FIG. 15C to illustrate this concept. This allows for equal loading in all directions. FIG. 15C shows discontinuous adhesive film regions to help explain this concept. Note the specific areas of the adhesive that are being utilized to provide the force depends on the direction of the retraction force provided by the anchored retractors.

Figure 15D:
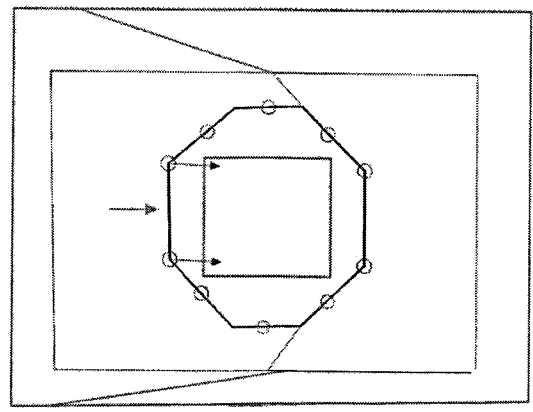
Figure 15E:
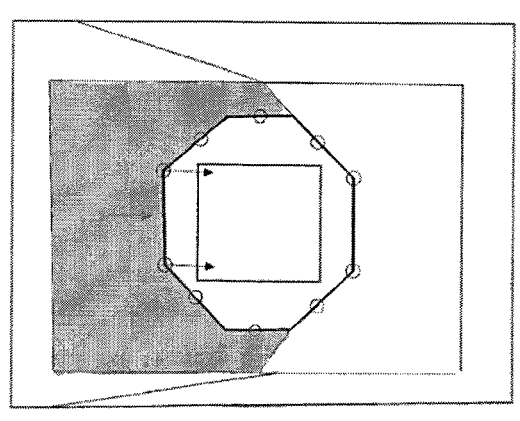

By connecting the individual adhesive films together as depicted in the drawings herein showing preferred embodiments of the retractor system, $F_{film}$ is further increased. The extent of the increase depends on the configuration the vectors and magnitudes of $F_{ret}$. Shown in the schematic view of FIGS. 15D and 15E is unilateral loading by two lateral $F_{ret}$. The shaded area of FIG. 15E illustrates the area of the adhesive/membrane that is being utilized when under load. This configuration illustrates the preferred embodiment as it will maximize $F_{film}$ regardless of the number of retractors, vectors, or loads.

Figure 16A:
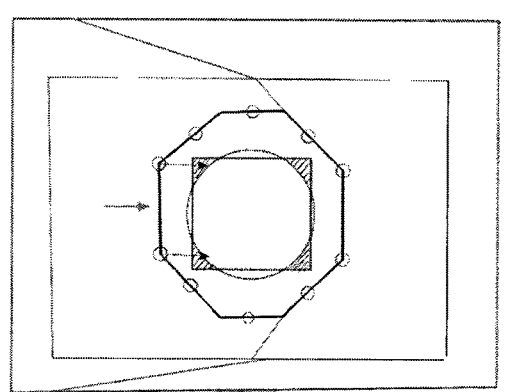
FIGS. 16A-16B are schematic views to illustrate the concept of how the inner adhesive film adds stability to the retractor of FIG. 11.
Figure 16B:
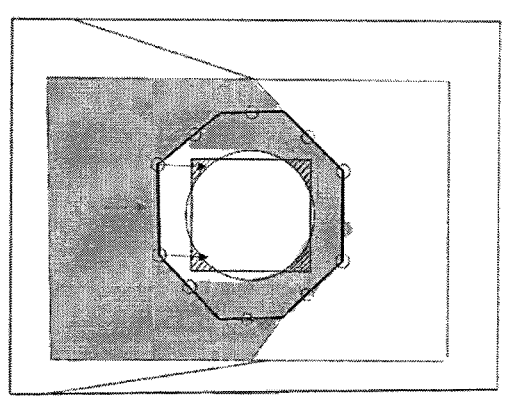
Figure 16B:
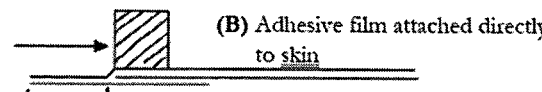
Figure 16B:
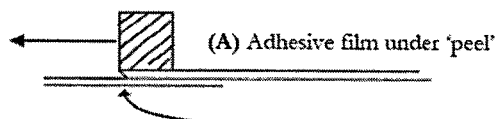

The area within the closed loop has also been optimized to maximize $F_{film}$ as well as minimize drape creep. The mechanism of this improvement differs from the aforementioned. The $F_{film}$ described previously was entirely in contact with the drape covering the patient. Within the inner diameter of the closed loop frame system there is both drape and the skin of the patient that lies adjacent to the operative site. Incorporating an inner adhesive film web within the inner periphery of the frame that allows contact to the patient's skin has a profound effect on drape creep. On the side of the frame that is being pulled away from the wound (A), the inside adhesive film provides stable anchoring to the relatively more stable skin of the patient, this is a similar effect as $F_{film}$ when attached to the Drape, but the friction coefficient is closer to 1. On the contralateral side of the loop the adhesive is in compression, which does not usually result in resistance. However, in many scenarios the skin layer may reach to the periphery of the rigid frame. In this case for the frame to move as a result of loading, it would require the adhesive film to be pulled off the patient at an angle of almost 180 degrees. This concept is illustrated in FIGS. 16A and 16B.

The combination of all these improvements yields an optimized drape geometry that maximizes stability by maximizing $F_{film}$ and minimizing the effects of $F_{drape}$. This configuration incorporates a frame in a loop with sufficient rigidity to translate loads, an adhesive film with sufficient area outside of the frame that is interconnected, and an inner web (membrane) with a sufficient area to allow for contact with the skin. The frame and stabilizing members of the various embodiments disclosed herein achieve this.

Note the stabilizing member with adhesive adherence having the foregoing characteristics/features can be used with the various frames disclosed herein as well as with other frames.

Turning now to a drape protection aspect of the present invention, in alternate embodiments, a drape protection layer can be provided. The drape protection layer can be utilized with any of the embodiments of the retractor systems disclosed herein as well as used with other retractor systems.

Figure 17:
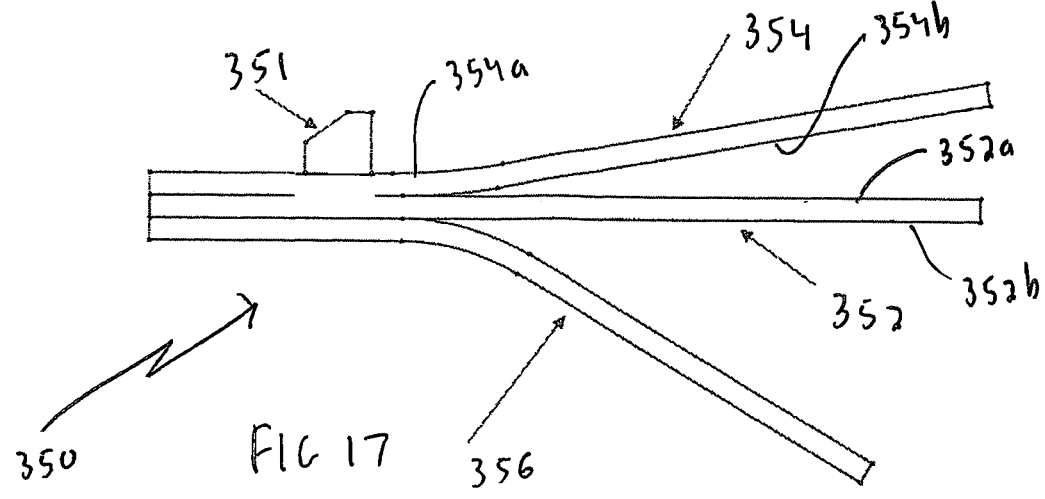
FIG. 17 is as side view showing the drape protection layer in accordance with some embodiments of the present invention.

During most surgical procedures, the retractor is removed prior to closure of the wound site and removing the drapes. If the device is stuck to a patient and drape, it can tear/rip the drape protecting the sterile field upon removal, or if it is excessively time intensive to remove carefully, it could result in delay of surgery or patient harm. This provides clinical challenges. Additionally, there may be times when the retractor needs to be relocated during the procedure or removed and replaced with a new retractor intraoperatively. The present invention in the embodiment of FIG. 17 provides a solution to facilitate retractor repositioning and removal. The retractor of FIG. 17 adds a protective layer, which a) allows for maximum adherence to the patient's skin and drape; b) allows for removal of the frame without disruption of the stabilizing member, and c) allows for another stabilizing member to be attached to it (i.e., replacing the frame of the device with another frame). Such removal is beneficial in certain clinical applications if a) the initial placement of the frame was not correct, e.g., due to an error or intraoperatively they find the surgery requires access to other tissue that is not within the confines of the initial frame; or b) post surgery, there is a desire move the frame out of the way for simpler wound closure or other clinical purposes. Removal of the frame can also make removing the bottom layer from skin/hair easier, faster and less traumatic to the patient. In either case, this feature for certain clinical applications reduces the potential hazard of breaking the sterile barrier provided by the drapes.

FIG. 17 shows a portion of the device 350 having a stabilizing (stability) member with two layers; a bottom (lower) layer 352 and a top (upper) layer 354. The bottom layer 352 is the layer that has adhesive on a bottom surface thereof to adhesively stick, i.e., provide adhesive adherence, directly to the patient or the drape. The bottom layer can alternatively attach or adhere to the patient or drape by other methods, adhesive providing one example. The bottom layer 354b of top layer 354 is adhesively attached to the top layer 352a of bottom layer 352. Attached/adhered to the upper surface 354a of top layer 354 is frame 351. The frame 351 can be attached to the top layer 354 by adhesive or other modes of attachment. Thus, the top layer 354 is positioned between the frame 351 and bottom layer 352. The frames can be of the type and configuration of those disclosed herein (e.g., living or mechanical hinges) or frames of other surgical retractors. That is, the multiple layer securement which provides a drape protection layer (also referred to here as a "rescue drape") can be adapted for use with retractor frames other than those of the present invention.

The handling layer 356 is attached to a lower surface 352b of bottom layer 352 to protect the adhesive until ready for use. The handling layer can be in the form a peel away layer that is manually "peeled off" the bottom layer 354 to expose the adhesive surface.

The layers 352, 354 are preferably attached in a manner that does not leave adhesive residue or adhesive resistance on the top of the bottom layer. This advantageously avoids surgical gloves and/or instruments from sticking/adhering to the exposed surface 352a of the bottom layer 352. In one embodiment this is achieved by the top layer 354 secured to the bottom layer 352 via surface tension alone (or by other modes of attachment), thereby leaving no residual adhesive residue once the frame and top layer are removed. Certain adhesives with reduced residue can alternatively be utilized to attach the layers 352 and 354.

The bottom and top layers 352, 354 (and handling layer 356) are pre-assembled, with tabs on the side to allow for easy separation of the frame/top layer assembly from the bottom layer 352.

In use, the handling layer 356 is peeled away exposing the adhesive surface on surface 352b of bottom layer 352 which is attached to the patient's skin or surgical drape. The bottom adhesive layer 352 and top layer 354 form the stabilizing member which functions in the same manner as the other stabilizing members disclosed herein, e.g., to distribute loads, provide counterforces, etc. to the loads/forces which are applied to the frame when retractors are attached to the anchoring members of the frame. If it is desired to remove and replace the frame, the top layer 354 (and attached frame 351) are removed from the bottom layer 352, leaving the bottom layer 352 adhesively secured to the patient or drape. Another frame, like the first frame, with a top and bottom layer is placed over the already positioned bottom layer 352, and the new bottom layer is secured to the first (already positioned) bottom layer by adhesive, i.e., adhesive on the bottom surface of the bottom layer of the second (replacement) device. Note the bottom layer can be cut through (incised) by the surgeon to access the surgical site. The top layer can also be cut through (incised) to access the surgical site.

Note the device can include the cuttable sheet. In some embodiments, the stabilizing membrane extends through the interior of the frame and thereby becomes the incise drape attached to the patient's skin and the surgeon would cut through the two layers of the membrane (top and bottom) or a single layer if the membrane has a single layer and then cut tissue. In some embodiments, the top layer is removed in manufacturing on the inside of the frame; leaving just the bottom layer as the incise drape which the surgeon would cut through. This could ease cutting since the surgeon would only need to cut through one instead of two layers. The other membranes disclosed in the other embodiments described herein could also, as explained above, serve as a drape through which the surgeon can cut to access the surgical site.

Figure 4:
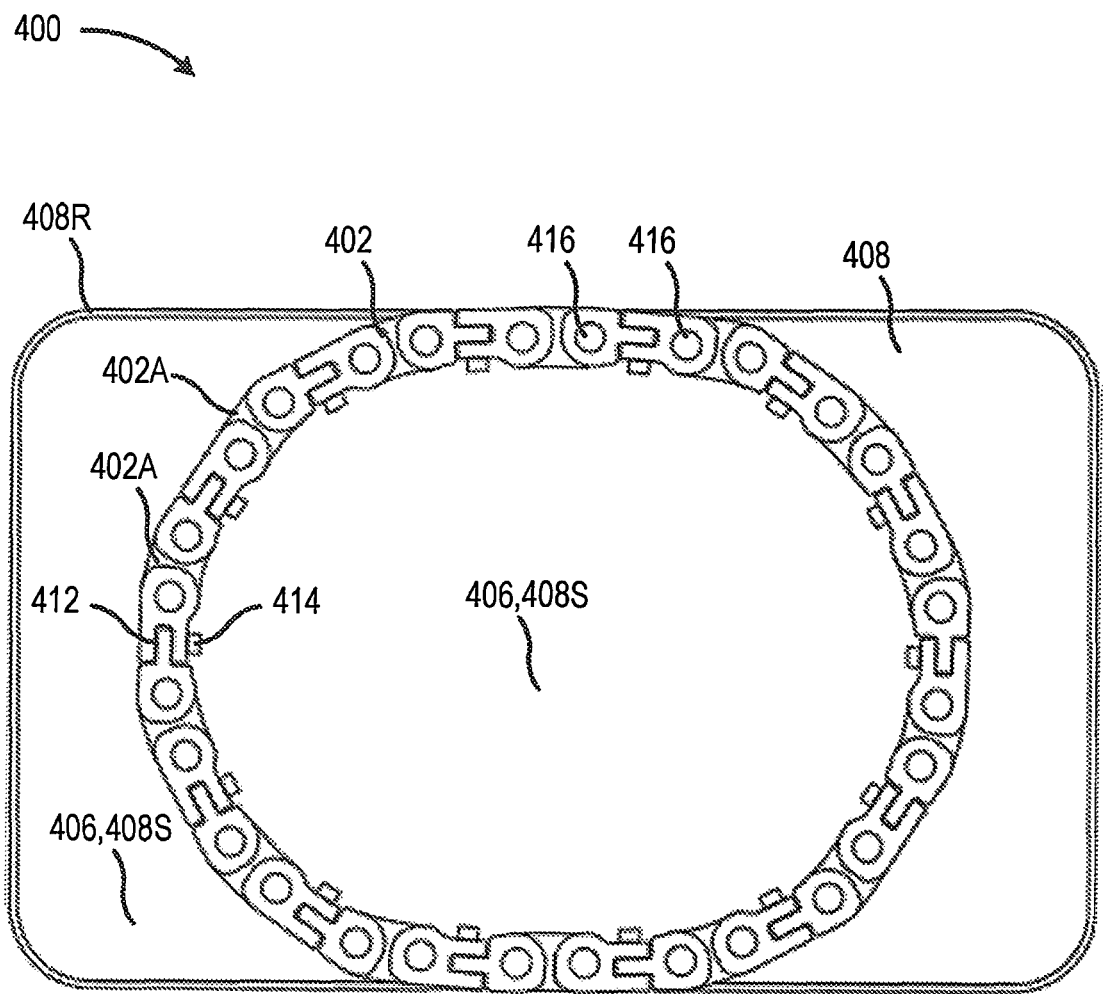
FIG. 4 is a top schematic view of an embodiment of the retractor system of the present invention having interlocking segments.
Figure 5A:
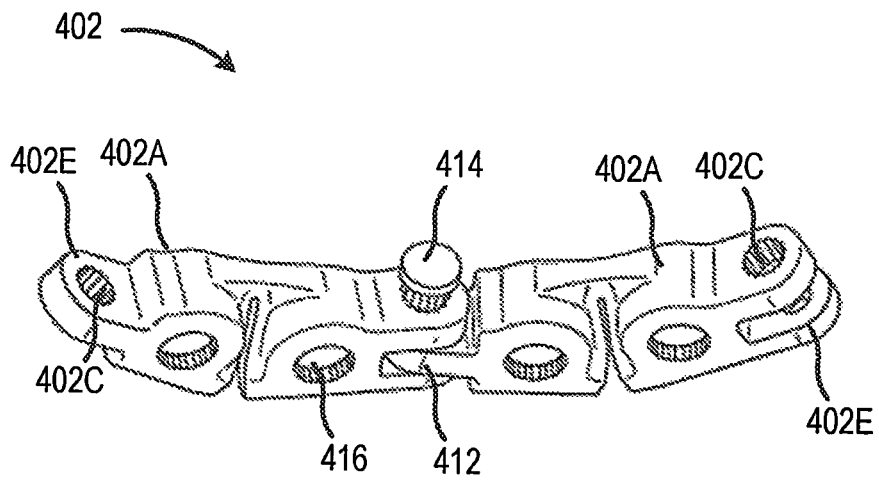
FIGS. 5A and 5B are close up perspective views of the interlocking segments of FIG. 4.
Figure 5B:
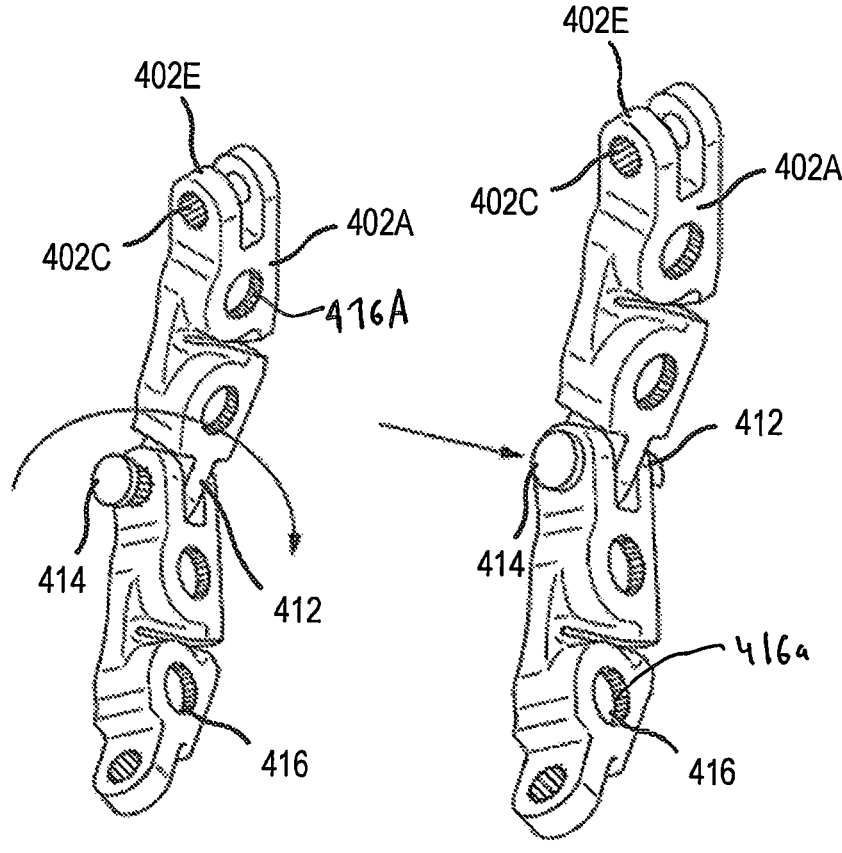
Figure 6:
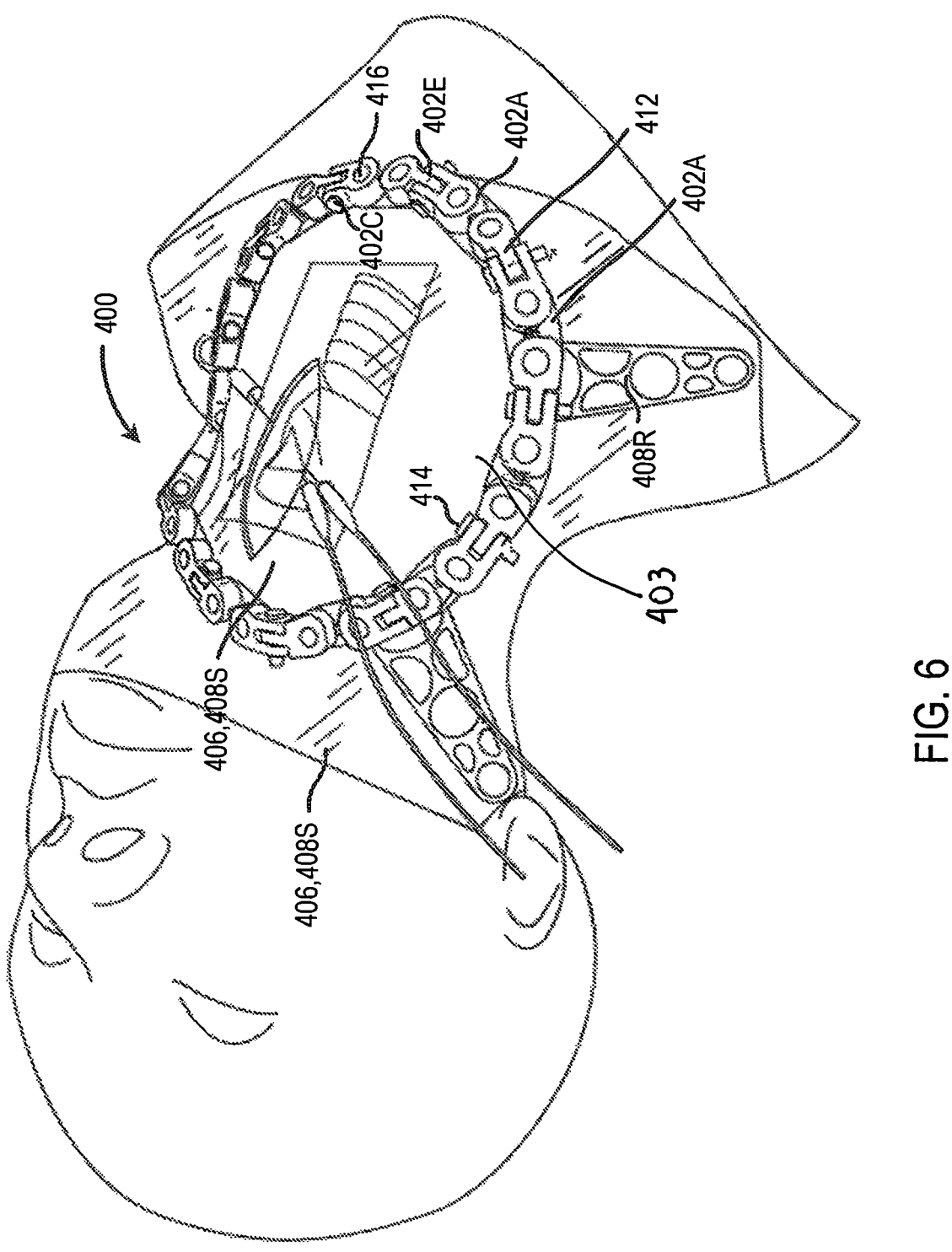
FIG. 6 is a perspective view showing the retractor of FIG. 5 in use on a neck area of a patient.

An alternate embodiment of the present invention having a mechanical hinge instead of a living hinge is illustrated in FIGS. 4-6. The mechanical hinges provide flexible joints which provide flexible sections of the frame positioned adjacent rigid sections. System 400 includes a frame 402 having a plurality of interlocking segments 402A. The interlocking segments 402A (also referred to herein as interlocking sections) can be rigid, flexible, or combinations thereof. The system 400 differs from the foregoing embodiments in the configuration and movement of the frame due to its interlocking segments forming a series of mechanical hinges along the frame. The adhesive layer(s) 406, stabilizing member(s) 408 (such as feature 408R and sheet 408S), etc., can be the same as the embodiments discussed above with respect to FIGS. 1A-1E and can in some embodiments include the aforedescribed rescue drape. The anchoring members for receiving/mounting retractor instruments can also be the same as in the foregoing embodiments. Therefore, for brevity, the discussion below focuses on the frame 402, it being understood that the stabilizing members, adhesive adherence, anchoring members, rescue drape, etc. as well as alternate embodiments thereof, discussed with respect to the other embodiments of the present disclosure are fully applicable to the embodiment of FIGS. 4-6.

Referring specifically to FIGS. 5A-5B, segments 402A include a plurality of end lock sections 402E configured to engage with adjacent end lock sections 402E. In some embodiments, end lock sections 402E are configured to reversibly engage with adjacent sections 402E. End lock sections 402E connect adjacent interlocking segments 402A at a joint 412 that allows pivoting of the individual segments with respect to each other. In some embodiments, the locking segments rotate in only one axis. End lock sections 402E include one or more cavities 402C. Cavities 402C are positioned and configured to accept locking features 414 to hold adjacent interlocking segments 402A together and lock adjacent interlocking segments 402A at a desired orientation relative to each other. In some embodiments, locking features 414 reversibly hold adjacent interlocking segments 402A together and reversibly lock adjacent interlocking segments 402A at a desired orientation relative to each other. This allows for unlocking of the segments. Frame 402 includes any suitable number of interlocking segments 402A, e.g., three, four, five, etc., and the number of segments shown in FIG. 4 provides one example. In some embodiments, frame 402 includes sufficient number of interlocking segments 402A to provide a closed configuration to fully encircle or surround a surgical site on a patient; in other embodiments, the interlocking segments can form an open configuration; e.g., U-shape, an arc of less than 360 degrees of a circle or oval, a bar shape (linear or angled), etc. so that the frame partially surrounds the surgical site.

Locking features 414 can be any suitable mechanism for holding adjacent interlocking segments 402A together and locking adjacent interlocking segments 402A at a desired orientation relative to each other. In some embodiments, locking features 414 include spline shafts, expanding clamshells, revolver shafts, sliding wedges, or combinations thereof. In the embodiments shown in FIGS. 5A-5B and FIG. 6, a plurality of spline shafts are used as locking features 414 for the adjacent segments. The spline shafts are inserted through aligned cavities 402C in engaged interlocking end lock sections 402E of adjacent interlocking sections 402A. As shown in FIG. 5B, the spline shafts have a first configuration that holds the adjacent interlocking sections 402A together, but permit them to rotate, i.e., pivot with respect to an adjacent section 402A, and a second configuration that substantially prevents them from rotating, e.g., locks them in position. The locking configuration rigidifies the frame while the unlocking configuration allows more flexibility of the frame.

With continued reference to FIGS. 4 and 5A-5B, interlocking segments 402A include one or more turret bases 416 disposed thereon, e.g., on a first surface. The turret bases 416 include openings 416a which are transverse to cavities 402c and axially spaced therefrom. Note one more of the interlocking segments 402A can have one or more turret bases 416 spaced apart along a length thus providing a plurality of turrets bases spaced circumferentially around the periphery, e.g., circumference of the frame 402. Turret bases 416 are configured to attach surgical tools to frame 402, e.g., via a friction fit, interference fit, mechanical lock, etc. Turret bases 416 are configured to releasably attach surgical tools to frame 402 such as surgical retractors or in some embodiments other instruments for assisting in the surgical procedure.

Figure 7:
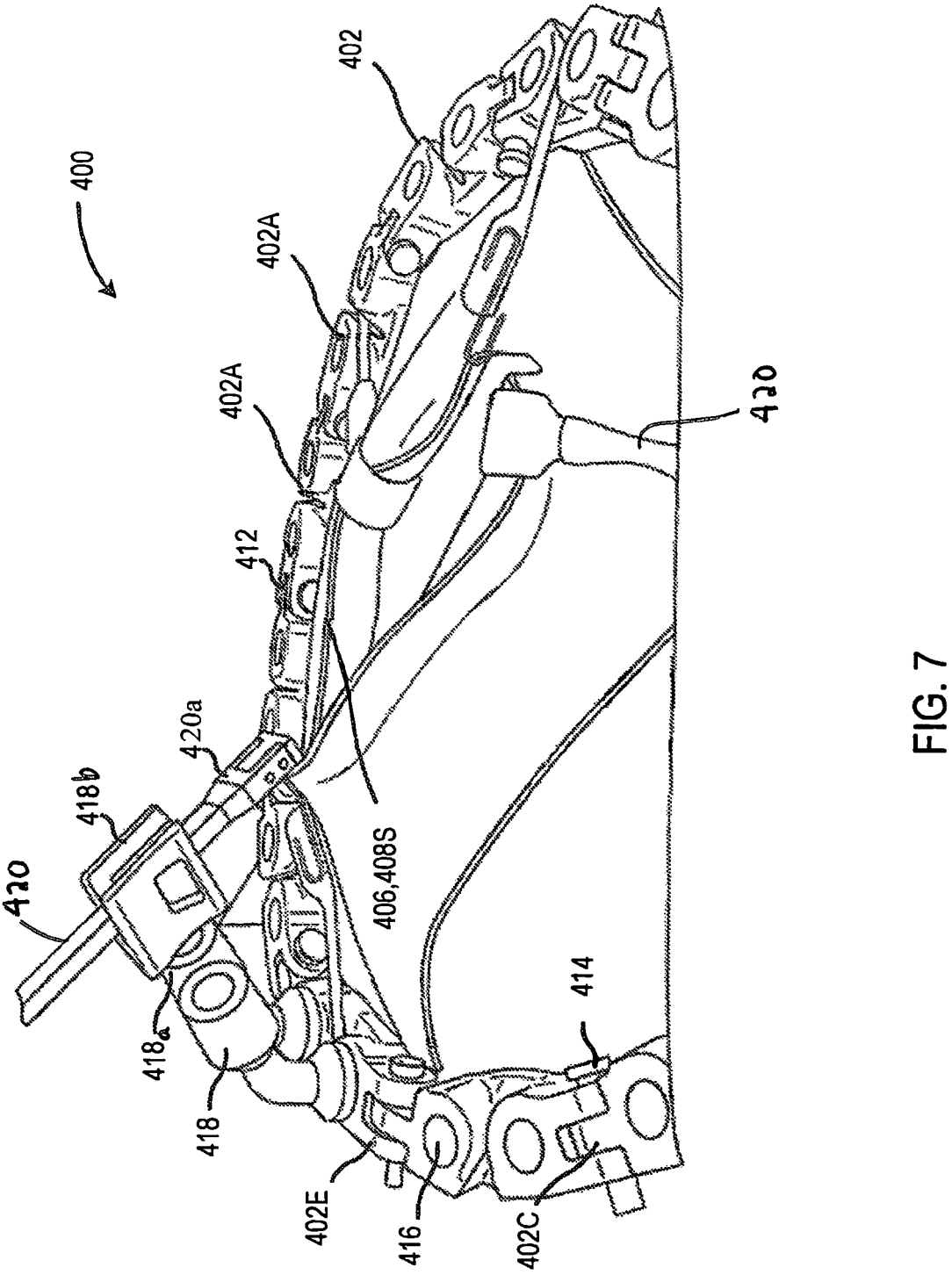
FIG. 7 is a side perspective view of an embodiment of the retractor system of the present invention having a turret tower attached thereto shown in use on a patient.

An exemplary embodiment of system 400 is shown in FIG. 7 with a variety of frame augmentations 418, e.g., surgical tools, positioned on frame 402. Frame augmentations 418 are configured to reversibly attach to frame 402 via a friction fit with a turret base 416, e.g., can extend to the turret base openings. Frame augmentations 418 can include anchor points (anchor members), turret towers, suture locks, suction guide turrets, powered illuminated components, or combinations thereof. The system 400 of FIG. 7 is shown incorporating a turret tower and having a retractor 420 attached thereto. The turret towers 418 can be flexible or rigid, and can have one or more bends for positioning the tissue retractors on other devices at particular angles. FIG. 7 also shows a second retractor approaching from another side of the frame 402, attached to a frame augmentation element 418 on another side of the frame (not shown). Note FIG. 7 shows the turret towers 418, 418a attached as one piece in accordance with some embodiments to provide further stabilization, e.g., limit or entirely prevent further bending of the tower when an instrument is attached so it can maintain the same angle. Ratchet or clamp 418b of tower 418a holds the instrument 420 proximal of tissue contacting end 420a. Note single turret towers rather than dual attached turret towers can be utilized.

During various surgical procedures it is oftentimes desirable to retract from a vector that is not necessarily lateral to the surgical incision and to limit contact of the retractors on a patient's skin. To accomplish this, turret towers allow for tissue retraction from deep to superficial along a variety of paths depending on the height and angle of the tower. Various angulations are available to allow conformity to patient specific anatomy. In preferred embodiments, the lengths, angulations, or combinations thereof, of the turret towers are adjustable. For example, to approach the site at a deeper angle, a turret tower can be provided at a different angle, achieved by the configuration of the tower and/or by the angle of attachment to the frame 402. It is envisioned that the turret tower can be movable within the opening 416a of the turret base 416 to pivot with respect to the turret base 16 to adjust its angle within the opening 416a or move up and down within the opening 416a, and in some embodiments, a locking mechanism or other arrangement can be provided to lock the turret tower in the desired position. The locking mechanism can be a separate component engageable with the base or tower or the tower and opening can be configured to interlock such as by rotation into a pin and slot arrangement. Other modes of securement of the turret tower in the desired position are also contemplated. The turret towers can also be removably mounted to the frame so turret towers of different sizes, angles or other configurations can be selectively attached at a desired site along the frame.

The towers can frictionally engage and retain the instrument via prongs/fingers similar to the notches described above which engage the shaft of the instrument as it extends through the notch between the prongs/fingers or have other configurations to provide a frictional engagement or the type of engagements to secure the instrument to the tower.

Frame 402 of system 400 conforms to a patient's specific anatomy, becomes rigid once conformation has been achieved, and maintains position and security throughout a surgical procedure. The frame 402 adheres to the patient's skin and/or drapes via an adhesive backing as discussed above. This frame enables flexible joints 412 (flexible sections), which provide mechanical hinges, to rotate freely and once the desired position of the adjacent interlocking segments 402A is achieved, pushing in on locking features 414 makes the joint rigid, e.g., no longer flexible in the plane substantially perpendicular to frame 402. This rigidifying of the frame to lock the mechanical hinges allows for fast engagement of system 400 as well as minimizing the overall size and bulk of frame 402. Once the locking features 414 have been engaged, the collection of interlocking segments 402A results in a rigid frame which conforms to the patient specific anatomy. The stabilizing member 403 of the system 400, attached to frame 402, distributes the load and counterbalances the forces applied to the retractor frame by the surgical instruments attached thereto in the same manner as the stabilizing members discussed in detail above. It should be appreciated that any of the stabilizing members discussed herein can be utilized with frame 402.

The system of FIGS. 4-7 can also include a modular, customizable, and reversibly assembled frame that provides greater visibility and multiple angles of approach while reducing the number of "hands" and clinicians to perform the surgery. The frames are assembled via quick and simple link locking and unlocking, e.g., via the insertable shafts, providing an advantage over threaded methods.

Methods and systems of the present disclosure are advantageous to provide an unobtrusive tissue retractor frame that is applied with stabilizing features and preferably adhesive layers that can be securely fixed to a patient. The system attaches to a broad range of surfaces including skin and/or surgical drapes and provides rigid support for easily attachable tissue retractors and other implements, resists unintentional movement, and yet can move with the patient if clinically required by flexing the frame as in the embodiment of FIGS. 1-3 or by unlocking segments of the frame as in the embodiment of FIGS. 4-7. The conforming frame lays above the patient's skin and remains in position by utilizing the stabilizing members and patient attachment/securement features, e.g., adhesive layers. The frame also has sufficient rigidity to resist lateral movements applied by retractors. Since the frame in the systems of the present disclosure is conforming and adhering to the patient's skin, system stability is maintained without removal of the device even when subject to joint manipulation during the procedure. A surgeon thus has the confidence that once in position the system and surgical retractors can be expected to remain in position, and the surgeon's efforts and energy can remain consistently focused on the surgical procedure, rather than adjusting and/or resetting surgical retractors. The frame and the stabilizing members have a low profile, so as not impede visibility of an incision site and not obstruct movements of the surgeon and their tools during a procedure. The system is also highly versatile, capable of use in a variety of surgical environments, from ophthalmic to spinal surgery. This versatility also reduces costs for the surgeon, as a single system can be useful across multiple surgical environments and patient sizes.

Attaching the frame directly to the skin/drapes also enables a low profile without sacrificing stability. The frames enable simultaneous, customizable, interchangeable mounting of multiple useful instruments, which is not only convenient but also results in fewer loose articles getting dropped or lost. By way of example, advantageous unilateral retraction at surgical sites, from deep to superficial retraction and allowing rigid tissue retractors to remain suspended above the patient's skin, e.g., by varying the height and angle of the retractor via one or more turret towers, is enabled.

Embodiments having a flexible protective sheet stabilizing member, positioned inside and outside the frame, provides maximal tractional stability when experiencing tensile loads, which can be optimized, e.g., by utilizing the combination of a frame and select sections of the stabilizing member (e.g., features such as paddles 108 of FIG. 1A) that are more rigid than the stabilizing sheet to translate forces throughout the system in order to maximize the available sheet that is in tension. Further, tensile and compressive loads are distributed over a broader surface, utilizing the patient's own anatomy as a support structure in a comprehensive stabilizing apparatus. Thus, otherwise inert areas of a patient have been repurposed to actively aid the surgeon at the incision site.

In various devices disclosed herein, the stabilizing member can extend inside the periphery of the frame and perform the additional function as a surgical drape to provide a sterile barrier. The stabilizing member can be incisable to access the surgical site.

Embodiments of the systems of the present disclosure reduce the risk of infection throughout a surgical procedure. The device can include a frame and a stabilizing member functioning as a surgical drape to protect the patient provided as a unit and can be applied to the wound location at the same time, typically when the surgical area is being prepped. It can also include an incise drape inside the periphery of the frame with a stabilizing member only outside the periphery or alternatively a stabilizing member inside the periphery of the frame over or under the drape (which is inside the frame periphery) and incisable with the drape. The incise drape can extend outside the periphery. The system can thus cover the majority of, if not all, the surgical site prior to skin incision. The sheet/incise drape and surgical drape thus act as a physical barrier to prevent bacterial transmission and protecting of the surface of the skin from accidental nicks and cuts from surgical instrumentation. Further, the sheet/incise drape and surgical drape may include broad-spectrum antimicrobial properties that neutralize bacterial pathogens, enhancing protection of the sterile barrier in the event the sterile field is compromised.

Although the systems, components, and methods described herein above relate to certain embodiments of the disclosure, those skilled in the art will readily appreciate that changes and modifications may be made thereto without departing from the spirit and scope of the present invention as defined by the appended claims. Persons skilled in the art will understand that the various embodiments of the disclosure described herein and shown in the accompanying figures constitute non-limiting examples, and that additional components and features may be added to any of the embodiments discussed herein without departing from the scope of the present invention.

It will be understood by those skilled in the art that the above particular embodiments are shown and described by way of illustration only. The principles and the features of the present disclosure may be employed in various and numerous embodiments thereof without departing from the scope and spirit of the invention as claimed. The above-described embodiments do not restrict the scope of the invention.

Additionally, persons skilled in the art will understand that the elements and features shown or described in connection with one embodiment may be combined with those of another embodiment without departing from the scope of the present invention.

As discussed above, the stabilizing members used with the various embodiments disclosed herein can be in the form of a membrane, a film, an adhesive film, struts, etc. Thus, although a particular embodiment might be discussed using a membrane or an adhesive film, other forms of the stabilizing member can alternatively be used with the frame of that particular embodiment. Also, an adhesive film in some embodiments can also be considered a type of membrane.

As discussed above, the stabilizing members can be attached to the patient or drape by methods/features other than adhesive to secure the stabilizing member to the patient or drape.

Throughout the present disclosure, terms such as "approximately," "about", "generally," "substantially," and the like should be understood to allow for variations in any numerical range or concept with which they are associated and encompass variations on the order of 25% (e.g., to allow for manufacturing tolerances and/or deviations in design). For example, the term "generally parallel" should be understood as referring to configurations in which the pertinent components are oriented so as to define an angle therebetween that is equal to 180°±25% (e.g., an angle that lies within the range of (approximately) 135° to (approximately) 225°) and the term "generally orthogonal" should be understood as referring to configurations in with the pertinent components are oriented so as to define an angle therebetween that is equal to 90° #25% (e.g., an angle that lies within the range of (approximately) 67.5° to (approximately) 112.5°).

The recitation of numerical ranges by endpoints includes all numbers within the range.

Although terms such as "first," "second," "third," etc., may be used herein to describe various operations, elements, components, regions, and/or sections, these operations, elements, components, regions, and/or sections should not be limited by the use of these terms in that these terms are used to distinguish one operation, element, component, region, or section from another. Thus, unless expressly stated otherwise, a first operation, element, component, region, or section could be termed a second operation, element, component, region, or section without departing from the scope of the present disclosure.

Each and every claim is incorporated as further disclosure into the specification and represents embodiments of the present disclosure. Also, the phrases "at least one of A, B, and C" and "A and/or B and/or C" should each be interpreted to include only A, only B, only C, or any combination of A, B, and C.

What is claimed is:

1. A device for surgical retraction comprising:
a frame having a lower surface, and an opposing upper surface and a periphery defining an interior space, the frame being flexible to conform to a patient's anatomy, the frame being non-linear in configuration and having a closed configuration, and including at least one anchoring member configured for retaining a tissue retraction member; and
a stabilizing member, the stabilizing member attached to the frame and securable to a patient, the stabilizing member underlying and attached to the frame at least along a majority of the periphery of the frame, wherein the tissue retraction member applying a force to the frame in a first direction is counterbalanced by the stabilizing member providing a force in a second opposite direction.

2. The device of claim 1, wherein net forces defined by simultaneous force in the first direction and the second direction are zero.

3. The device of claim 1, wherein the stabilizing member extends one or both of a) laterally outwardly from the periphery of the frame or b) laterally inwardly from the periphery of the frame toward an incision site into the interior space, the stabilizing member providing an adherence surface to an area larger than an area covered by the frame.

4. The device of claim 1, wherein the frame has a first side and a second side opposite the first side, the first and second sides each having first and second flexible sections and a rigid section between the first and second flexible sections.

5. The device of claim 4, wherein corners of the frame are more rigid than the flexible sections.

6. The device of claim 4, wherein the at least one anchoring member is positioned at the rigid section of the frame.

7. The device of claim 1, wherein the stabilizing member has a region laterally inward of the frame incisable to access a surgical site.

8. The device of claim 1, wherein e stabilizing member is adhesively secured to the patient, and further nprises a removable protective layer, the protective layer removable to expose adhesive for adhesive securement of the stabilizing member to skin of the patient or to a surgical drape positioned over the patient.

9. The device of claim 1, wherein the frame is configured to allow deformation in a plane perpendicular to a surface of the patient's anatomy and resist deformation in a plane parallel to the surface of the patient's anatomy.

10. The device of claim 1, wherein the at least one anchoring member comprises a notch configured to frictionally retain the tissue retraction member, the notch having a V-shape tapering in a direction toward the stabilizing member.

11. The device of claim 10, wherein the notch is configured to not open further during flexing of the frame.

12. The device of claim 1, wherein the stabilizing member includes antimicrobial agents carried thereon.

13. The device of claim 1, wherein the at least on anchoring member comprises a plurality of fingers spaced apart about the periphery and configured to frictionally maintain the tissue retraction member positioned between the fingers, the at least one anchoring member extending laterally outwardly of an outermost edge of the frame and in a direction non-parallel to a plane of the frame.

14. A device for surgical retraction comprising:

a frame having a periphery, a lower surface and an opposing upper surface, the frame flexible to conform to a patient's anatomy, the frame including at least one anchoring member extending therefrom for retaining a tissue retraction member;

a stabilizing member attached to the frame, the stabilizing member adhering to a skin of a patient or a surface overlying the skin of the patient to secure the frame, wherein the stabilizing member is adhesively secured to the patient; and a removable protective layer including a first peel away layer a nd a second peel away layer, the second peel way layer having a first portion extending outwardly o irst region of the first peel away layer ind a second porti twardly of a second opposite region of the first peel away layer he first and second portio ng on opposin z ends of the stabilizing member such that first and second regions of the fir peel away er to the center of the stabilizing member than the first and second portions way layer, the protective layer removable to expose adhesive for adhesive securement of the stabilizing member to skin of the patient or to a surgical drape positioned over the patient, wherein the first peel away layer is removed prior to the second peel away layer to provide adhesive sect rement prior to removal of the second peel away.

15. The device of claim 14, wherein the at least one anchoring member includes a notch formed in a rigid section of the frame adjacent a living hinge of the frame.

16. The device of claim 15, wherein the notch tapers in a direction toward the stabilizing member.

17. The device of claim 14, wherein the stabilizing member is underlying and attached to the frame at least along a majority of the periphery of the frame.

18. The device of claim 14, wherein the first peel away layer and the second peel away layer are in contact prior to removal.

19. A device for surgical retraction comprising:

a frame having a lower surface, and opposing upper surface and a periphery defining an interior space, the frame being flexible to conform to a patient's anatomy, the frame including at least one anchoring member configured for retaining a tissue retraction member; and a continuous stabilizing member, the stabilizing member underlying and attached to the frame along at least the periphery and securable to a patient, wherein the tissue retraction member applying a force to the frame in a first direction is counterbalanced by the stabilizing member providing a force in a second opposite direction, wherein the stabilizing member has a region laterally inward of the frame extending inwardly of the periphery and incisable to access a surgical site.

20. The device of claim 19, wherein the stabilizing member is adhesively secured to skin of the patient or a surgical drape positioned over the patient.

21. The device of claim 19, wherein the frame has first and second flexible sections and a rigid section between the flexible sections.

* * * * *